(12) United States Patent
Cho et al.

(10) Patent No.: US 10,842,688 B2
(45) Date of Patent: Nov. 24, 2020

(54) ABSORBENT ARTICLE WITH ELEVATED SKIN-CONTACTING TOPSHEET LAYER

(71) Applicant: Kimberly-Clark Worldwide, Inc, Neenah, WI (US)

(72) Inventors: MoonYoung Cho, Yongin-Si (KR); HyungByum Kim, Seoul (KR); JuHyung Lee, Yongin-Si (KR); HyungWoo Park, Yongin-Si (KR); SeongDae Roh, Yongin-Si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 728 days.

(21) Appl. No.: 15/540,199

(22) PCT Filed: Dec. 30, 2014

(86) PCT No.: PCT/US2014/072714
§ 371 (c)(1),
(2) Date: Jun. 27, 2017

(87) PCT Pub. No.: WO2016/108833
PCT Pub. Date: Jul. 7, 2016

(65) Prior Publication Data
US 2017/0354549 A1 Dec. 14, 2017

(51) Int. Cl.
*A61F 13/515* (2006.01)
*A61F 13/472* (2006.01)
*A61F 13/511* (2006.01)

(52) U.S. Cl.
CPC .......... *A61F 13/515* (2013.01); *A61F 13/472* (2013.01); *A61F 13/47218* (2013.01); *A61F 2013/51195* (2013.01)

(58) Field of Classification Search
CPC ................ A61F 13/512; A61F 13/5123; A61F 2013/5127; A61F 2013/5128;
(Continued)

(56) References Cited

U.S. PATENT DOCUMENTS 5,007,906 A 4/1991 Osborn, III et al.
5,062,840 A * 11/1991 Holt ...................... A61F 13/495
604/385.19
(Continued)

FOREIGN PATENT DOCUMENTS

AU 703676 B2 4/1999
CN 1079139 A 12/1993
(Continued)

OTHER PUBLICATIONS

Howarth, Helena et al., "Visual Depictions of Female Genitalia Differ Depending on Source," Journal of Medical Ethics: Medical Humanities, vol. 36, 2010, pp. 75-79.
(Continued)

*Primary Examiner* — Michele M Kidwell
(74) *Attorney, Agent, or Firm* — Kimberly-Clark Worldwide, Inc.

(57) ABSTRACT

An absorbent article includes two planar liquid permeable topsheet layers with a first topsheet layer suspended from the longitudinal ends of the second topsheet layer. The first topsheet layer is of shorter length than the second topsheet layer such that the relaxed absorbent article includes a curvature along its length. The first topsheet layer defines a central opening and two end openings which allow for air circulation through the article and also for the second topsheet layer to be seen through the openings in the first topsheet layer. While the first topsheet layer is at least extensible, it is desirably elastic.

24 Claims, 8 Drawing Sheets

(58) Field of Classification Search
CPC .............. A61F 13/472; A61F 13/47218; A61F 13/515; A61F 2013/51195; A61F 13/5116
See application file for complete search history.

(56) References Cited

U.S. PATENT DOCUMENTS

| | | | |
|---|---|---|---|
| 5,324,278 | A | 6/1994 | Visscher et al. |
| 5,425,726 | A | 6/1995 | Shimizu et al. |
| 5,593,400 | A | 1/1997 | Oleary |
| 5,674,214 | A | 10/1997 | Visscher et al. |
| 5,853,403 | A | 12/1998 | Tanzer et al. |
| 5,885,268 | A | 3/1999 | Bien et al. |
| 6,114,597 | A | 9/2000 | Romare |
| 6,293,935 | B1 | 9/2001 | Kimura et al. |
| 6,296,628 | B1 | 10/2001 | Mizutani |
| 6,371,948 | B1 | 4/2002 | Mizutani |
| 6,423,043 | B1 | 7/2002 | Gustafsson |
| 6,471,682 | B2 | 10/2002 | Kashiwagi |
| 6,508,795 | B1 | 1/2003 | Samuelsson et al. |
| 6,585,712 | B2 | 7/2003 | Yoshimasa |
| 6,652,498 | B1 | 11/2003 | Glasgow et al. |
| 6,676,649 | B2 | 1/2004 | Mizutani |
| 6,913,599 | B2 | 7/2005 | Mishima et al. |
| 7,033,341 | B2 * | 4/2006 | Mishima .............. A61F 13/4942 604/385.01 |
| 7,160,278 | B2 | 1/2007 | Mizutani et al. |
| 7,598,427 | B2 | 10/2009 | Ragnarson et al. |
| 7,947,027 | B2 | 5/2011 | VanDenBogart et al. |
| 7,976,525 | B2 | 7/2011 | McDaniel |
| 8,048,049 | B2 | 11/2011 | Fujikawa et al. |
| 8,383,877 | B2 | 2/2013 | Singh et al. |
| 8,513,483 | B2 | 8/2013 | Tee, Jr. et al. |
| 10,213,347 | B2 * | 2/2019 | Miao .................. A61F 13/5125 |
| 10,667,960 | B2 * | 6/2020 | Kim .................. A61F 13/53743 |
| 10,758,427 | B2 * | 9/2020 | Nakayama ........ A61F 13/49009 |
| 2002/0050001 | A1 | 5/2002 | Takai et al. |
| 2002/0058919 | A1 | 5/2002 | Hamilton et al. |
| 2002/0072726 | A1 * | 6/2002 | Mishima .............. A61F 13/4942 604/385.22 |
| 2002/0120247 | A1 | 8/2002 | Mizutani et al. |
| 2002/0143309 | A1 | 10/2002 | Glasgow et al. |
| 2002/0151860 | A1 | 10/2002 | Klemp et al. |
| 2005/0027278 | A1 | 2/2005 | Mizutani et al. |
| 2008/0065038 | A1 * | 3/2008 | Sugiyama ........ A61F 13/49473 604/385.04 |
| 2009/0247978 | A1 | 10/2009 | Boissier |
| 2012/0277711 | A1 | 11/2012 | Kim et al. |
| 2013/0197462 | A1 | 8/2013 | Abuto et al. |

FOREIGN PATENT DOCUMENTS

| | | |
|---|---|---|
| CN | 1082872 A | 3/1994 |
| CN | 10827871 A | 3/1994 |
| CN | 1440263 A | 9/2003 |
| JP | 01-122727 U | 8/1989 |
| JP | 2002-315776 A | 10/2002 |
| JP | 2007-167191 A | 7/2007 |
| KR | 1995-0036309 A | 10/1995 |
| KR | 2000-0057870 A | 9/2000 |
| WO | WO 1997/007764 A1 | 3/1997 |
| WO | WO 1999/045872 A1 | 9/1999 |
| WO | WO 2003/075813 A1 | 9/2003 |
| WO | WO 2014/085974 A1 | 6/2014 |

OTHER PUBLICATIONS

Lloyd, Jillian et al., "Female Genital Appearance: 'Normality' Unfolds," BJOG: An International Journal of Obstetrics and Gynaecology, vol. 112, Issue 5, May 2005, pp. 643-646.

Neumann, A.W., and R.J. Good, "Techniques of Measuring Contact Angles," Chapter 2, Surface and Colloid Science—Experimental Methods, vol. 11, edited by R.J. Good and R.R. Stromberg, Plenum Press, 1979, pp. 31-91.

* cited by examiner

ABSORBENT ARTICLE WITH ELEVATED SKIN-CONTACTING TOPSHEET LAYER

FIELD OF THE INVENTION

The present invention is generally directed to absorbent personal care articles. In particular, the present invention is directed to feminine and adult hygiene absorbent personal care articles, such as liners, pads, briefs, garments, diapers and their associated skin-contacting layers (or topsheet layers), as well as methods for producing such articles.

BACKGROUND OF THE INVENTION

Feminine and adult hygiene absorbent personal care articles are often used to protect consumer undergarments and outergarments from soiling, and to collect and retain body exudates such as menses, blood, or urine. Such articles are most commonly placed in the crotch region of garments during use. In the context of such products, absorbency and comfort are two main product attributes and areas of concern for the users of such articles. In particular, users are often interested in knowing that such products will sufficiently absorb body exudates in order to protect their garments, or bedsheets from staining. Users are also interested in having such products demonstrate reduced feelings of wetness once a product has been soiled or insulted during use. Unfortunately, once such a product has been soiled, the topsheet layer (i.e. user-facing, skin-contacting surface layer of the article) often remains wet or at least feels wet for some time throughout the period of use. The topsheet layer may frequently be absorbent, being made so from hydrophilic construction materials, such as natural fibers or surfactant-treated polymeric materials. These materials often retain at their surface some noticeable moisture following soiling, thereby creating the uncomfortable wetness sensation during their continued use. While in an ideal situation, such articles are replaced by the user or caregiver once soiling actually occurs, in some instances the user or caregiver may not initially recognize that soiling has occurred. Upon such realization, the user may not be in a location where a change of product is possible or convenient. The frequent replacement of these articles may also be impractical given a user's particular daily activities even if wetness is detected immediately following soiling.

As a result of the desire of consumers to experience a reduced wetness sensation from a product during prolonged use (for both skin-health rationale as well as physical comfort), manufacturers have explored numerous technological approaches to address these feelings following product insult. Manufacturers have attempted to reduce both the initial feelings of wetness and also continuing sensations of "rewet". For the purposes of this application, the term "rewet" refers to the propensity of personal care absorbent articles to absorb fluid or liquid such as menses or urine through the topsheet layer and deliver it to an article interior and subjacent absorbent layer, and subsequently, to release it under the continuing pressure of wear, back to the topsheet layer from the absorbent layer(s). This release of fluid/liquid back to the topsheet layer often leads to the consumer perception of continuing wetness.

Absorbent article manufacturers have specifically designed individual topsheet layers for reduced wetness (and rewet), based on chemical enhancements to the topsheet layer. In this regard, hydrophobic topsheet layers have been developed from polymeric fibrous nonwoven layers or apertured film layers, such that the article demonstrates an extended feeling of dryness at the article skin-contacting surface. Further, absorbed fluid that is retained in absorbent layers subjacent these topsheet layers may have less of a propensity to pass back through the topsheet layer to the user's skin, as a result of the hydrophobic interior surface properties of the topsheet. In some instances, the topsheet layer acts as a one-way valve, allowing moisture to pass in one direction and keeping it below the user-facing, skin contacting surface.

Such topsheet designs have included relatively small or larger openings to allow for the direct passage of fluid to an underlying absorbent layer. For example, Australian Patent 703676 to Nomura et al. describes a topsheet layer that is attached to a pad's longitudinal direction ends and transverse direction side edges, with an exposed central opening, to allow for fluid to pass into the product. While such designs have been somewhat successful in creating a longer consumer feeling of dryness, there is still a need for products which offer increased breathability and air circulation, and increased consumer confidence and perception that such product will physically separate the user from the fluid in the absorbent layer(s), with less likelihood that the consumer will actually experience a continuing feeling of wetness, either as a result of initial soiling or rewet. The topsheet layer construction in AU 703676 provides for a skin-contacting surface layer that lies adjacent a secondary topsheet layer and underlying absorbent structure, with no predictable spatial gap between layers other than side pockets. Further, hydrophobic, film-based topsheets with relatively larger openings, have often provided an uncomfortable, "plastic"-like feel to the products, and there is a continuing need to address this undesirable sensation. Also, in such products with relatively larger openings in a topsheet layer that are closely associated with subjacent absorbent structures, as such products frequently move or shift about in an undergarment during a user's daily activities, such topsheet layers may have a propensity to move out of direct contact with the user's genital or perineal region (in totality, or at specific locations, such as out of contact with the area surrounding the user's vagina), ultimately leading to less capture of bodily fluids or exudates that might be released by a user's body.

Manufacturers have also developed multicomponent topsheet layers in which the layer incorporates different materials at different regions across the user-facing, skin-contacting surface. In such layers, a first material can either be side-by-side with a second material along a product central longitudinal direction, or alternatively, can surround a second different material, as seen for example, in JP 1-122727U. Such layers include two materials generally within the same X-Y plane, and which have been designed in-part, for the user to feel different sensations at a centrally located, fluid-deposition region (or insult region) on the article, compared with at the article peripheral side edges. In such designs for example, apertured polymeric films may be placed in the product's centrally located region with softer nonwoven materials placed at the product's peripheral side edges. In some patent references, such multicomponent topsheet layers are described as being placed above a macro-apertured subjacent layer, when viewed along an article depth direction, such as for example in international publication WO 2014/085974 to Miao Lin et al. However, even with such so-called, "dual-cover", "multicomponent", or "bicomponent" topsheets, there is still a need for increased breathability and air circulation in absorbent articles, and specifically in-and-around topsheet layer edges. There is also still a need for physical separation along the article depth direction, of the topsheet layer from the underlying absorbent layers so as to reduce rewet possibilities and enhance user confidence. There are further needs for such topsheet layers that maintain contact or close association with the genital or perineal region of a user's body, despite other article layers moving with a user's undergarments during daily activities.

Since hydrophobic and multicomponent topsheet layers have only offered a partial solution to the initial wetness or continuing rewet sensations, absorbent article manufacturers have also explored more complex structural solutions, as opposed to individual layer or material design to address user concerns. For example, manufacturers have created fluid distribution systems to more rapidly or effectively transfer fluid away from the initial fluid insult region of an article topsheet. However, such systems have not satisfactorily addressed surface retention of fluid in topsheet layers, nor assisted in physically separating the topsheet layers from underlying soiled structures.

Manufactures have therefore also designed structures to physically separate initially soiled regions of an article, from the one or more subjacent absorbent layer(s), or to otherwise isolate the absorbed fluid in the absorbent article from the fluid deposition area. Such physical separation has often been accomplished at greater cost and article complexity, through the use of rigidifying spacing layers or structures, or multiple material types. Spacing layers may be seen for instance, in U.S. Pat. No. 5,324,278 to Visscher et al., which describes use of a spacing or separating hump-like structure positioned between a topsheet and subjacent absorbent core layer, and U.S. Pat. No. 6,296,628 to Mizutani and U.S. Pat. No. 7,160,278 to Mizutani et al., which describe a compound-like pad in which an upper spaced absorbent structure is positioned over a lower absorbent pad structure. In such compound pads, the raised topsheet layer is still maintained immediately adjacent or attached to an absorbent layer, thereby allowing moisture to potentially re-contact a user's skin during continued use. Such raised layers may also sacrifice user-comfort, as the user may feel relatively rigid protrusions in the female perineal area during use.

Other elevated liquid-handling layers have been designed for a variety of absorbent articles in order to create a spatial gap between an underlying absorbent layer and the user-facing liquid handling layer. In U.S. Pat. No. 5,853,403 to Tanzer et al. for example, such an apertured, elevated liquid handling layer is illustrated. Such layer is connected across the layer and article longitudinal direction ends (and in some examples, along the lateral side edges), and is designed to handle a relatively large amount of liquid. Further auxiliary or floating structures are illustrated in JP2007167191 to Tanaka, United States Publication 20050027278 to Mizutani et al. and U.S. Pat. No. 6,423,043 to Gustafsson. However, these structures either encompass multiple additional materials that necessitate additional and costly manufacturing steps and provide a potential source of discomfort to a user; encompass a variety of continuous attachment mechanisms; or alternatively position an upper, user-facing surface immediately adjacent an additional liquid handling or absorbent layer. Therefore, there is still a need for an absorbent article which physically separates a topsheet layer from an absorbent layer, without reliance on additional and costly intermediate layers or structures, and as a result, reduces rewet and encourages breathability and air circulation through the article while in use.

Finally, in U.S. Pat. No. 6,913,599 to Mishima, an upper, centrally apertured and stretchable, liquid impervious skin-facing layer is placed on a diaper-like undergarment. However, such elevated, apertured layer is fully attached to the garment across both the longitudinal ends and lateral side edges, minimizing airflow along an article's longitudinal ends, especially considering such skin-facing layer is described as being liquid impervious. There is therefore a need for an absorbent article which provides also for peripheral air circulation from all sides of a product's peripheral side edges.

SUMMARY OF THE INVENTION

In a first embodiment, an absorbent article has a longitudinal direction, a transverse direction, and a depth direction. The absorbent article has absorbent article opposing first and second longitudinal direction ends, and absorbent article opposing lateral side edges extending between the absorbent article opposing first and second longitudinal direction ends. The absorbent article further includes a liquid permeable first topsheet layer having a first topsheet layer relaxed length, first topsheet layer opposing longitudinal direction ends, and first topsheet layer opposing lateral side edges extending between the first topsheet layer opposing longitudinal direction ends. The liquid permeable first topsheet layer defines a liquid permeable first topsheet layer opening and is at least extensible, and alternatively elastic, along at least the absorbent article longitudinal direction. The absorbent article further includes a liquid permeable second topsheet layer subjacent to the liquid permeable first topsheet layer along the absorbent article depth direction. The liquid permeable second topsheet layer has a second topsheet layer relaxed length that is longer than the first topsheet layer relaxed length. The liquid permeable first topsheet layer is attached by attachment zones to the liquid permeable second topsheet layer at the liquid permeable first topsheet layer opposing longitudinal direction ends. The liquid permeable second topsheet layer can be viewed through the liquid permeable first topsheet layer opening. The absorbent article further includes a liquid impermeable backsheet layer subjacent to the liquid permeable second topsheet layer along the absorbent article depth direction and at least one absorbent core layer sandwiched between the liquid permeable second topsheet layer and the liquid impermeable backsheet layer. The absorbent article further includes at least two opposing longitudinal direction end openings at or adjacent the absorbent article opposing longitudinal direction ends, the longitudinal direction end openings formed by portions of the liquid permeable first topsheet layer.

In a second embodiment, the absorbent article includes a liquid permeable first topsheet layer that is attached on the absorbent article by at least four separate attachment zones, at least two of the attachment zones being positioned either at or adjacent each absorbent article opposing longitudinal direction end, such that at least one end opening in the liquid permeable first topsheet layer is defined by the liquid permeable first topsheet layer at or adjacent each of the liquid permeable first topsheet layer opposing longitudinal direction ends, and between the at least two attachment zones. In yet another alternative embodiment, the absorbent article includes a central longitudinal direction and the opposing longitudinal direction end openings number at least two which are positioned along the central longitudinal direction. In still a further alternative embodiment, the opposing longitudinal direction end openings are selected from curvilinear-edged, semicircular, or U-shaped opening configurations. In another alternative embodiment, the at least two opposing longitudinal direction end openings are aligned with each other along the absorbent article central longitudinal direction. In a further alternative embodiment, the liquid permeable first topsheet layer attachment zones are spaced inwardly from the absorbent article opposing longitudinal direction ends. In still another alternative embodiment, the liquid permeable first topsheet layer attachment zones are spaced inwardly of the liquid permeable second topsheet layer opposing longitudinal direction ends. In yet another alternative embodiment, the liquid permeable first topsheet layer and the liquid permeable second topsheet layer each include peripheral edges at or adjacent the absorbent article opposing longitudinal direction ends, which peripheral edges are of generally similar shape for each of the liquid permeable first and second topsheet layers.

In still another alternative embodiment, the peripheral edges of each topsheet layer at or adjacent the absorbent article opposing longitudinal direction ends are of generally the same size. In another alternative embodiment, the liquid permeable first topsheet layer includes at least one centrally positioned opening. In another alternative embodiment, the absorbent article includes a central longitudinal direction and the centrally positioned opening is selected from the group consisting of oval-shaped, circular shaped, oblong, and multiple proximate openings positioned along the absorbent article central longitudinal direction between the opposing longitudinal direction end openings. In still a further alternative embodiment, the absorbent article includes an apertured layer having a centrally positioned aperture, the apertured layer situated between the liquid permeable second topsheet layer and the absorbent core layer in the absorbent article depth direction, and further wherein the centrally positioned aperture is aligned along the absorbent article depth direction with the centrally positioned opening. In another embodiment, the centrally positioned opening and the centrally positioned aperture are both oval-shaped. In still another embodiment, the absorbent article includes more than one opposing longitudinal direction end opening defined by the liquid permeable first topsheet layer at or adjacent each of the absorbent article opposing longitudinal direction ends.

In still another alternative embodiment, the liquid permeable first topsheet layer is attached to a layer subjacent to it along the absorbent article depth direction, at or adjacent at least one location along the absorbent article opposing lateral side edges. In yet another embodiment, the liquid permeable first topsheet layer is attached to a layer subjacent to it along the absorbent article depth direction, at or adjacent substantially the entire length of the absorbent article opposing lateral side edges.

In another alternative embodiment, the liquid permeable first topsheet layer is elastic, such as along the article longitudinal direction. Such elastic topsheet layer may be fashioned from a single elastic layer or an elastic laminate layer, such as for example a stretch-bonded elastic laminate layer. Such stretch-bonded elastic laminate layer may be formed from a stretched film bonded to one or more inelastic nonwoven layers while the film is in a stretched configuration, or alternatively, to a stretched nonwoven web or series of strands (such as preformed fibers/yarn or extruded strands) that are bonded to one or more inelastic nonwoven layers while the stretched nonwoven web or series of strands are in a stretched configuration. Such stretched bonded laminates are elastic in the article longitudinal direction at least, but may also be elastic in the article transverse direction. Such first topsheet layer may therefore be extensible or elastic in the article longitudinal direction, or alternatively in both the longitudinal and transverse direction.

In still another alternative embodiment, the liquid permeable second topsheet layer is a multicomponent topsheet layer having a central topsheet section and side topsheet sections, in which the central topsheet section of the liquid permeable second topsheet layer can be seen through an opening in the liquid permeable first topsheet layer without a visual hindrance of an intermediary layer. In yet another embodiment, the liquid permeable first topsheet layer is hydrophobic. In a further alternative embodiment, a topographical visual feature on a layer subjacent the liquid permeable first topsheet layer in the absorbent article depth direction, can be seen through at least one opening of the liquid permeable first topsheet layer. In still another embodiment, the liquid permeable first topsheet layer is separable from the liquid permeable second topsheet layer by a distance of between about 0.0 mm and about 6 mm, alternatively between about 0.01 mm and about 6 mm during article use.

In another embodiment, the liquid permeable first topsheet layer is attached to the liquid permeable second topsheet layer only at the liquid permeable first topsheet layer opposing longitudinal ends, and the liquid permeable second topsheet layer includes a curved configuration when the absorbent article is in a relaxed configuration. In still another embodiment, an absorbent article includes multiple topsheet layers, a backsheet layer and an absorbent core layer sandwiched between one of the topsheet layers and the absorbent core layer. The absorbent article particularly includes a first planar, liquid permeable topsheet layer and a second planar, liquid permeable topsheet layer, both the first planar, liquid permeable topsheet layer and the second planar, liquid permeable topsheet layer have a substantially elongate shape with a longitudinal direction and a transverse direction, each liquid permeable topsheet layer comprising two opposing longitudinal ends. The first planar, liquid permeable topsheet layer is desirably extensible, alternatively elastic, and defines a centrally positioned opening and at least two opposing longitudinal end openings therein, whereby the second planar, liquid permeable topsheet layer is visible through the centrally positioned opening and at least two opposing longitudinal end openings. The first planar, liquid permeable topsheet layer is suspended between the opposing longitudinal ends of the second planar, liquid permeable topsheet layer, whereby the two liquid permeable topsheet layers are mutually joined solely at or adjacent their opposing longitudinal ends. The second planar, liquid permeable topsheet layer is curved in the longitudinal direction such that a void space is present between the first planar, liquid permeable topsheet layer and the second, planar liquid permeable topsheet layer. In such embodiment, the first planar, liquid permeable topsheet layer has a length which is less than the length of the second planar, liquid permeable topsheet layer when both topsheet layers are in a relaxed state. In an alternative embodiment, the first planar, liquid permeable topsheet layer is in a pretensioned state within the absorbent article. Alternatively, the first planar, liquid permeable topsheet layer is elastic. Still in a further embodiment, the first planar, liquid permeable topsheet layer is hydrophobic and the second planar, liquid permeable topsheet layer is at least partially hydrophilic. Still in a further embodiment, the first planar, liquid permeable topsheet layer is formed from a single elastic sheet or an elastic laminate, alternatively a stretch bonded elastic laminate.

In yet another embodiment, the absorbent article has a longitudinal direction, a transverse direction, and a depth direction, said absorbent article having absorbent article opposing first and second longitudinal direction ends, and absorbent article opposing lateral side edges extending between the absorbent article opposing first and second longitudinal direction ends. Such an absorbent article includes a liquid permeable first topsheet layer having first topsheet layer opposing longitudinal direction ends, and first topsheet layer opposing lateral side edges extending between the first topsheet layer opposing longitudinal direction ends. The liquid permeable first topsheet layer defines a liquid permeable first topsheet layer opening. The liquid permeable first topsheet layer is elastic along at least the absorbent article longitudinal direction. A liquid permeable second topsheet layer is subjacent to the liquid permeable first topsheet layer along the absorbent article depth direction. The liquid permeable second topsheet layer is attached by attachment zones to the liquid permeable second topsheet layer at the liquid permeable first topsheet layer opposing longitudinal direction ends, such that the attachment of the liquid permeable first topsheet layer to the liquid permeable second topsheet layer imparts a curvature to the absorbent article towards the liquid permeable first topsheet layer. The liquid permeable second topsheet layer can be viewed through the liquid permeable first topsheet layer opening. The absorbent article also includes a liquid impermeable backsheet layer subjacent to the liquid permeable second topsheet layer along the absorbent article depth direction and at least one absorbent core layer sandwiched between the liquid permeable second topsheet layer and the liquid impermeable backsheet layer. Such absorbent article further includes at least two opposing longitudinal direction end openings at or adjacent the absorbent article opposing longitudinal direction ends, with the longitudinal direction end openings formed by portions of the liquid permeable first topsheet.

BRIEF DESCRIPTION OF THE DRAWINGS

A full and enabling disclosure of the present invention is set forth more particularly in the remainder of the specification, including reference to the accompanying figures, in which.

DEFINITIONS

Figure 1:
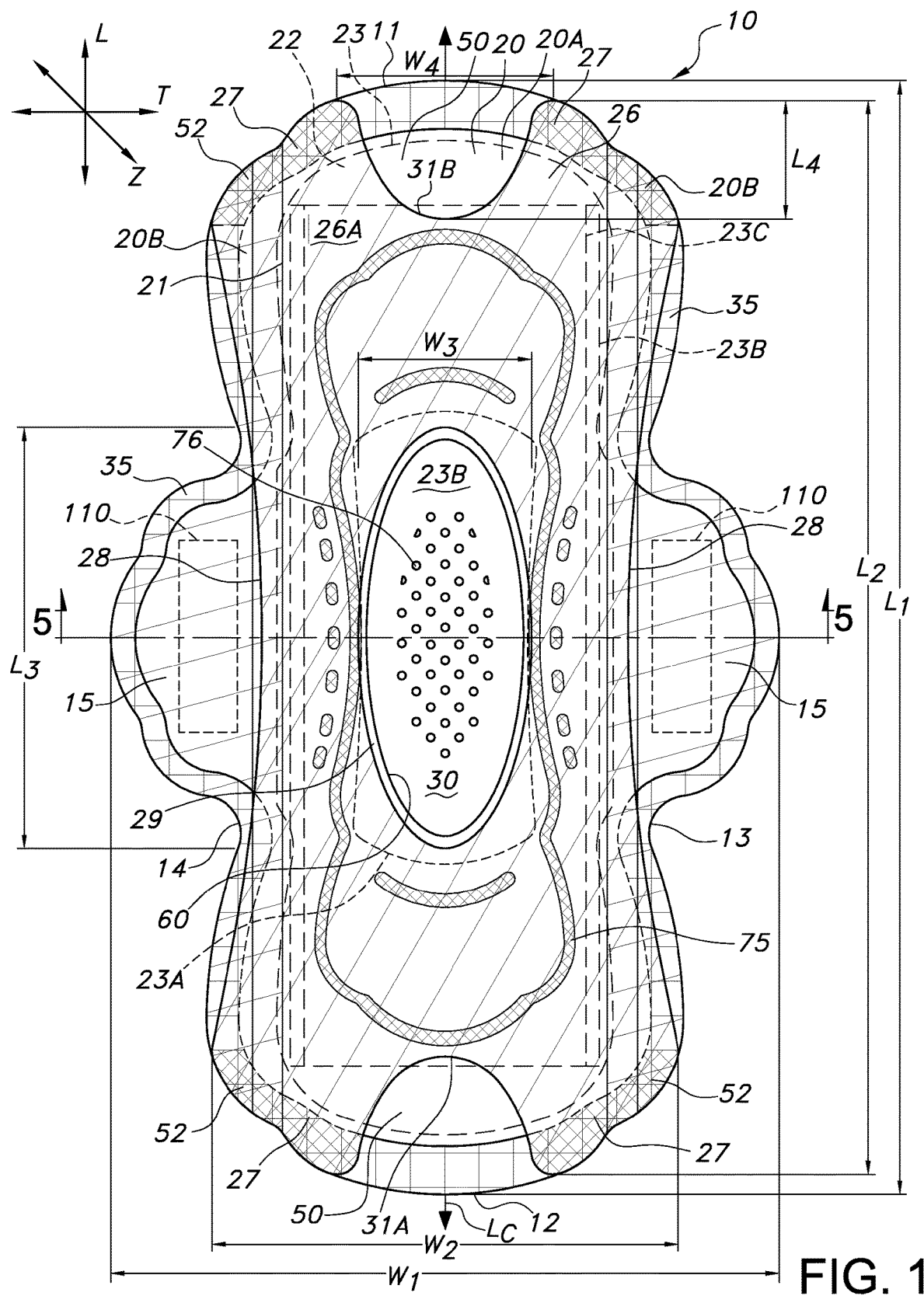
FIG. 1 illustrates a top plan view of a feminine care absorbent personal care article in accordance with the invention, in the form of a sanitary pad.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, hydroentangling, and bonded carded web processes (such as through-air bonded carded webs or TABCW).

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Butin, et al., which is incorporated herein in its entirety by reference thereto. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto. Spunbond fibers are generally not tacky when they are deposited onto a collecting surface. Spunbond fibers may sometimes have diameters less than about 40 microns, such as between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 5,284,703 to Everhart, et al., and U.S. Pat. No. 5,350,624 to Georger, et al., each of which are incorporated herein in their entirety by reference thereto.

As used herein, the term "storage component" refers to an absorbent article layer which primary function is designed to ultimately store body exudate in the form of liquid/fluid waste. That is, such storage component is an absorbent layer designed to retain aqueous-based liquid/fluid, after the liquid has been received into an absorbent article through a topsheet layer, and optionally through liquid handling layers such as surge, transfer, and distribution layers. Such storage component layer may include for example, superabsorbent materials (or SAPs) as are known in the absorbent article art, but generally includes all or primarily hydrophilic materials such as cellulosic wadding, or other cellulosic-based materials, porous foams, or other hydrophilic liquid retaining materials for example. A liquid/fluid storage component is to be distinguished from a topsheet layer, or an intermediate liquid/fluid handling layer such as a surge, transfer, distribution, or directing layer, that are each designed as "pass-through" layers to perform a function on liquid as it passes from an initial liquid/fluid receiving layer to the fluid storage component. Pass-through layers pass liquid through the layer as it travels to its ultimate storage destination. Examples of various functions of a pass-through layer may be to slow down liquid flow, to spread the flow of liquid along multiple directions on an adjacent layer, to channel fluid quickly to a lower layer within an article, or to perform a specific separation operation or treatment on the liquid, as it passes through the layer to a storage layer. An initial liquid/fluid receiving layer (ie topsheet layer) of an absorbent article having at least a topsheet layer, absorbent core layer, and backsheet layer (i.e. at least the first, user-facing topsheet layer of a multilayered absorbent article in the article depth direction), shall not be considered a "storage component" for the purposes of this application. The incidental presence of initially received liquid/fluid on a topsheet layer, or the rewet of such topsheet layer, shall not for the purposes of this application, constitute ultimate liquid storage. Desirably, in one embodiment such topsheet layer retains little to no liquid. In an alternative embodiment, such topsheet and any directly attached layer thereto that is attached across substantially most (greater than 50%) of the topsheet garment-facing underside surface along the topsheet layer length, retains little to no liquid. Desirably, in a further embodiment, such topsheet layer and any optional, directly attached layer are manufactured entirely from hydrophobic materials. Desirably in one embodiment, such topsheet layer does not include any other layer attached to it, except at its opposing longitudinal direction ends, with such other attached layer being a secondary topsheet layer.

As used herein, the terms "stretchable" and "extensible" shall be interchangeable and generally refer to a material that stretches or extends in the direction of an applied force (e.g., cross-machine direction or CD, or machine direction or MD) by about 50% or more, in some embodiments about 100% or more, and in some embodiments, about 200% or more of its relaxed length or width. The term "machine direction" means the direction in which either the material or article is made and often refers to the longitudinal direction of an article or material. The term "cross-machine direction" means the direction perpendicular to the machine direction, and often refers to the transverse direction of an article or material.

As used herein, the term "elastic" generally refers to an extensible material that, upon application of a stretching force, is stretchable in at least one direction (e.g., CD or MD), and which upon release of the stretching force, contracts/returns to approximately its original dimension. For example, the stretched material may contract or recover at least about 50%, and even more desirably, at least about 80% of its stretched length. It should be understood that an extensible material may lack recovery properties such that it is considered an "inelastic" material. An elastic material would be extensible, but an extensible material may not be elastic. Further, for the purposes of this application, the liquid permeable first topsheet layer is at least extensible along the absorbent article longitudinal direction (machine direction), and is desirably elastic along the absorbent article longitudinal direction. In an alternative embodiment, such first topsheet layer is extensible and/or elastic in both the absorbent article longitudinal and transverse directions.

Material may be tested for its elastic properties using a cyclical testing procedure. In particular, 2-cycle testing may be employed to 100% defined elongation. For this test, the sample size may be 3 inches (7.6 centimeters) in the cross-machine direction by 6 inches (15.2 centimeters) in the machine direction. The grip size may be 3 inches (7.6 centimeters) in width. The grip separation may be 4 inches (10.2 centimeters). The samples may be loaded so that the machine direction of the sample is in the vertical direction. A preload of approximately 20 to 30 grams may be employed. The test may pull the sample to 100% elongation at a speed of 20 inches (50.8 centimeters) per minute and then immediately (without pause) return the sample to 0% elongation at a speed of 20 inches (50.8 centimeters) per minute. The results of test data are desirably from the first and second cycles. The testing may be performed on a Sintech Corp. Constant rate of extension tester 2/S with a Renew MTS mongoose box (control) using TESTWORKS 4.07b software (Sintech Corp., of Cary, N.C.) and conducted under ambient conditions.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "absorbent article" refers herein to a garment or other end-use personal care/hygienic absorbent article, including, but not limited to, catamenial products, such as sanitary napkins and pads, overnight feminine pads, pantiliners, and panty shields, incontinence pads, diaper devices, and the like.

As used herein, the term "hydrophobic" shall refer to a material having a contact angle of water in air of at least 90 degrees. The terms "hydrophilic" and "wettable" are used interchangeably to refer to a material having a contact angle of water in air of less than 90 degrees. The phrase "more hydrophilic" shall refer to a material having a relatively lower contact angle. The phrase "more hydrophobic" shall refer to a material having a relatively higher contact angle. Hydrophobicity and hydrophilicity can both be the result of the inherent properties of the composition making up a material. For example, polyolefinic and/or elastomeric polymers are typically hydrophobic, while cellulosic materials are typically hydrophilic. Alternatively, such properties may be the result of coatings that have been added to base substrates.

For the purposes of this application, contact angle measurements can be measured using a Cahn SFA-222 Surface Force Analyzer System, or a substantially equivalent system. Contact angles can be determined as set forth in Neumann, A. W., and R. J. Good, "Techniques of Measuring Contact Angles," Chapter 2, Surface and Colloid Science—Experimental Methods, Vol. 11, edited by R. J. Good and R. R. Stromberg, Plenum Press, 1979, pp. 31-91, which is hereby incorporated by reference in a manner that is consistent herewith. For coated substrates, contact angle measurement may be made in accordance with ASTM D-7334, titled "Standard Practice for Surface Wettability of Coatings, Substrates and Pigments by Advancing Contact Angle Measurement". Such advancing contact angle measurement is preferred unless otherwise noted. Examples of hydrophobic surface treatments that may be used to coat particular topsheet layers include those described in United States patent publication 2013/0197462 to Abuto et al., which is hereby incorporated by reference thereto for purposes not inconsistent herewith.

For the purposes of this application, the terms "ultimate elongation" or "ultimate extension" shall be synonymous, and shall refer to the maximum allowable extension capability of a layer along the absorbent article longitudinal direction, prior to compromise of layer integrity (such as by separation, rupturing, ripping, or tearing).

For the purposes of this application, the term "macro opening" shall refer to the centrally positioned opening and/or end openings of various layers in an absorbent article. Such openings shall in one embodiment encompass cut-out or punched hole features.

In one embodiment, at least the macro-opening(s) and optionally the second topsheet layer user-facing surface (through the opening(s)) are visible to an individual article user from at least the range of about 0.25 feet (0.075 meters) to about 3 feet (0.91 meters), when viewing the user-facing, topsheet surfaces of the absorbent article. In an alternative embodiment, such macro-openings are normally visible to an article user from a distance of at least 3 meters without opening background color contrast (that is contrast between the opening and the immediately surrounding article surfaces), or 5 meters, with opening background color contrast. The term "macro-opening" shall not encompass microholes or interstitial spaces that may be present in a topsheet layer material, such as the ordinary interstitial spaces formed between fibers of a nonwoven web, or the microapertures that may be present in vacuum apertured films.

Figure 2:
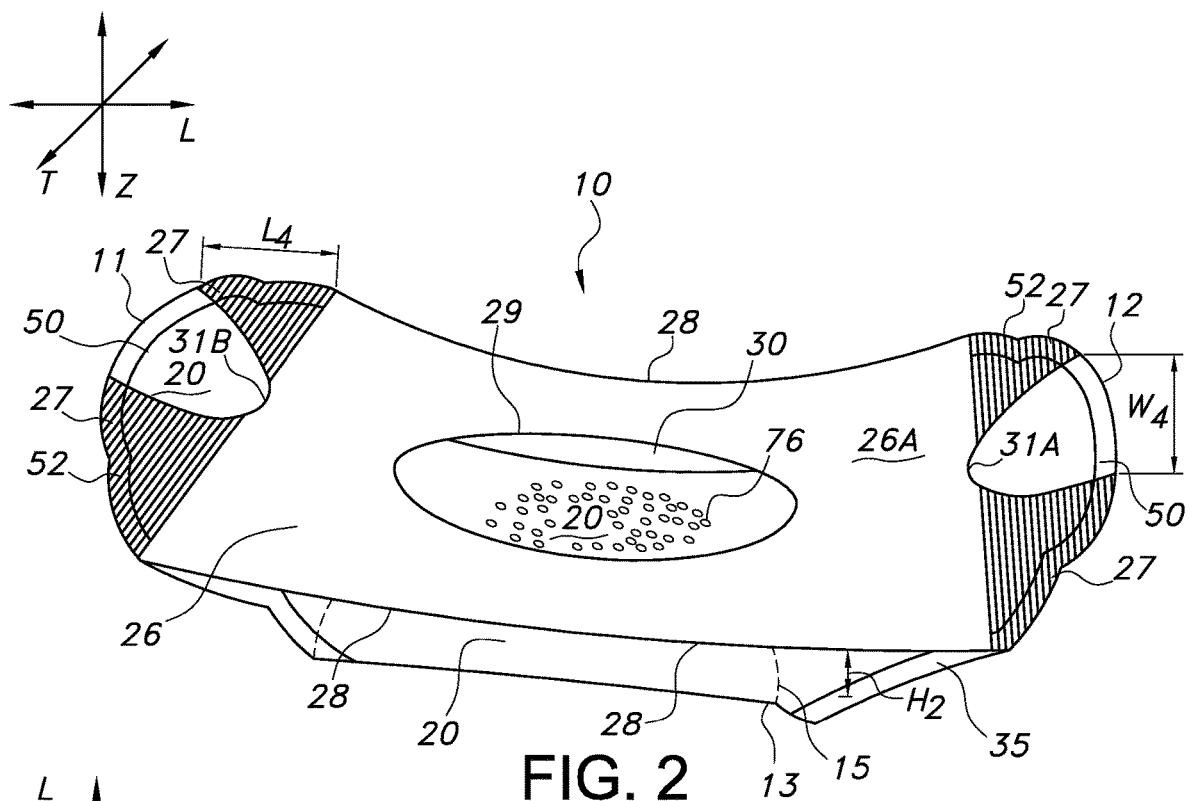
FIG. 2 illustrates a top perspective view of a different embodiment of a sanitary pad with wings folded under the pad opposing lateral side edges.
Figure 2A:
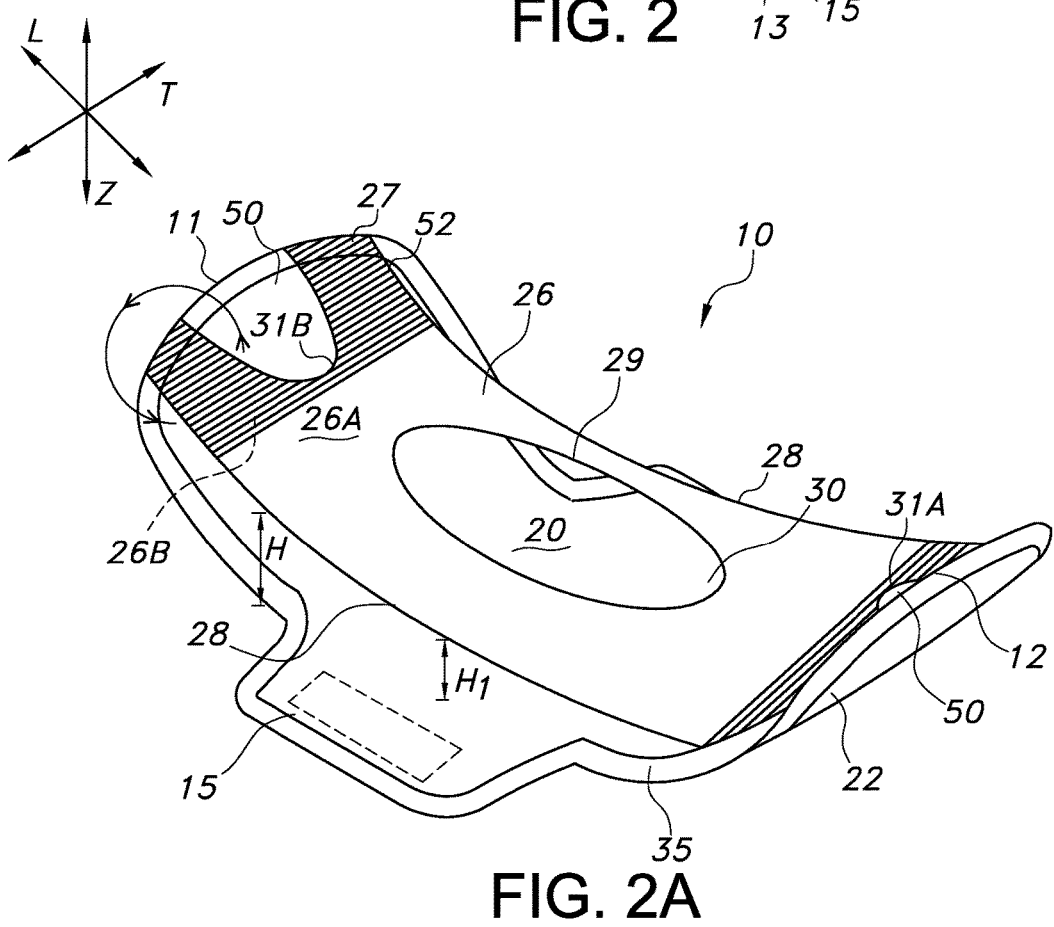
FIG. 2A illustrates a top perspective view of a different embodiment of a sanitary pad with wings positioned outwardly from the pad opposing lateral side edges.
Figure 2B:
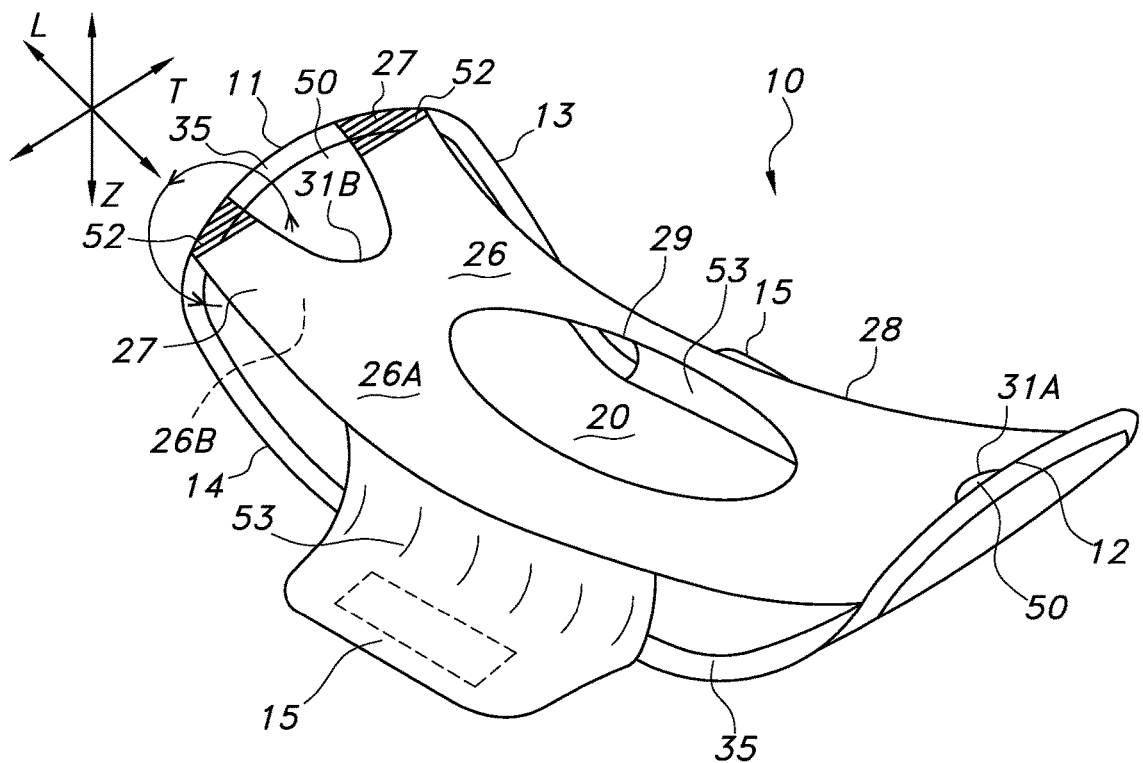
FIG. 2B illustrates a top perspective view of a different embodiment of a sanitary pad with wings positioned outwardly from the opposing lateral side edges, and including limited topsheet layer attachments along the absorbent article opposing lateral side edges.
Figure 2C:
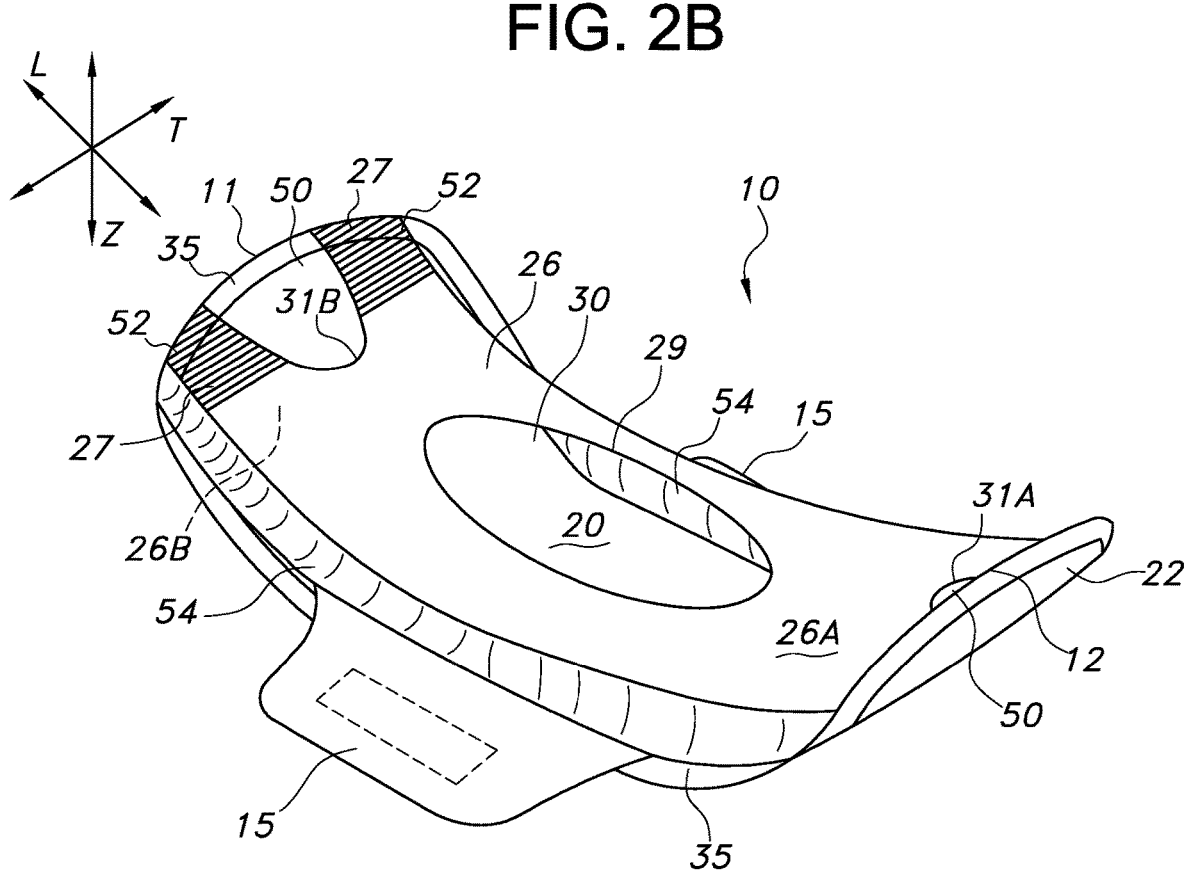
FIG. 2C illustrates a top perspective view of a different embodiment of a sanitary pad with wings positioned outwardly from the opposing lateral side edges, and including continuous topsheet layer attachments along the absorbent article opposing lateral side edges.

As used herein, the term "relaxed" shall refer to the condition of either an article or layer (as specified), when it is laid in an open configuration on a level, planar (flat) surface (such as a desktop), with the article user-facing surface facing upwards and without any externally derived tension or pressure being exerted on any of its article, or layer surfaces. That is, a relaxed article would be one that was placed on a flat, level surface in an open configuration with the user-facing surface directed upwards. An example of such an article configuration is illustrated in FIGS. 2A-2C. Such a relaxed condition of an "article", does not for the purposes of this application, imply that the entire article lies flat against the flat surface. A relaxed "layer" would be one that was placed on a flat, level surface, in a flat condition, with the user-facing surface directed upwards. Such is exemplified by the layer in FIG. 4.

As used herein, the term "liquid permeable" shall refer to a material which is porous and which is water permeable due to the flow of water and other aqueous liquid or fluid through the pores. The pores are large enough and frequent enough to permit leakage and flow of liquid water. "Liquid impermeable" shall refer to a material that does not allow water or aqueous liquid/fluid to pass through it under ordinary use conditions.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not illustrated in most figures except where additional location emphasis is desired, it should be understood that traditional absorbent article construction adhesive (or other bonding technology) is to be used to fasten the various layers of the described articles together. Such construction adhesive or other bonding technology is desirably placed so as not to interfere with the flow of fluid/liquid waste through the article, such as in the depth direction towards the absorbent core layer, or in a location so as not to interfere with or impede the occurrence of desired spatial gaps or void spaces as noted. For example, adhesive or other bonding techniques are desirably used only between or at, the peripheral side edges of immediately subjacent layers so as to avoid interfering with liquid flow and to preserve spatial gaps (thereby avoiding unnecessary subjacent layer contact in specific regions). In noted absorbent article areas where void spaces are potentially present, adhesive or other bonding features would be desirably absent or present in limited amounts.

Generally speaking, the absorbent personal care articles of the present invention are ideally suitable for use as hygiene articles in the feminine and adult care product categories. Such articles include for example, feminine hygiene sanitary pads and liners, and adult care garment inserts, pads, and liners. While pads are illustrated in the figures, it should be understood however, that the invention is not meant to be limited to such product applications. For instance, baby and child care product applications are similarly contemplated to be within the scope of the term "absorbent articles".

In order to provide absorbent hygiene articles with both attributes of absorbency and comfort, it has been found that absorbent articles with an elevated skin-contacting top sheet layer that allows for continuous close contact with a user's body of the elevated layer despite movement of an undergarment are desirable. Desirably, such articles provide for predictable air circulation through multiple ventilation end openings and spatial gaps between multiple topsheet layers. Such openings along multiple (and desirably four) sides/edges of the article enable reduction of rewet sensations. Further, through the use of elastically separated topsheets, likelihood of a continuous separation of a body insult from a user's skin during prolonged article use is increased.

Such an elevated, skin-contacting topsheet layer acts as a suspended or "floating" layer above a lower absorbent portion of the article. The elevated, skin-contacting topsheet layer is extensible, and desirably elastic, and may be attached to the remaining portion of the article either only at, or adjacent to the opposing longitudinal direction ends of the article; alternatively, at or adjacent such ends and also partially along discrete areas of the article opposing lateral side edges; or in a further embodiment, at or adjacent such ends and the entire opposing lateral side edges of the absorbent article. Such opposing lateral side edge attachment may be by a relatively vertical standing, wall-like barrier layer (at each opposing lateral side edge near an article wing feature), which extends to the elevated, skin-contacting topsheet layer from the remaining subjacent structure of the absorbent article. Alternatively, such wall-like barrier layer may be an expandable wall-like structure, which expands during article use.

In any event, such elevated, skin-contacting topsheet layer (the "upper" first topsheet layer) is itself liquid permeable aside from any macro-openings present in the layer, and desirably includes at least a centrally positioned macro-opening for unobstructed flow of liquid to a lower, spaced-apart absorbent portion of the article from the user's body. The elevated skin-contacting layer is desirably soft to the touch but not wettable. Desirably, such elevated layer does not contain aqueous liquid/fluid absorbent material, since it maintains constant contact with the user's body throughout use. Nor does the elevated layer have directly attached thereto any liquid/fluid storage component. The lower, spaced-apart absorbent portion of the article is covered by a "lower" liquid permeable second topsheet layer beneath the first topsheet layer. In one embodiment, such lower, liquid permeable second topsheet layer is physically separated from the liquid permeable first topsheet layer except at its longitudinal ends, so as to create a void space desirably along the entire length, or substantially the entire length of the first topsheet layer. In one embodiment, the lower liquid permeable topsheet layer does not touch the user's body except through occasional contact in the centrally positioned macro-opening of the first topsheet layer, or end openings of the first topsheet layer. If the first topsheet layer is narrower in the article transverse direction than the second topsheet layer, additional contact may occur. The potential void space between the topsheet layers appears and disappears according to body movements. However, the preferably elastic nature of the elevated, skin-contacting topsheet layer (and preferably prestretched-condition of the layer at the time that it is bonded to the ends of the pad), creates a predisposition of the upper topsheet layer to return to the spaced apart configuration over a period of prolonged article use. If such liquid permeable first topsheet layer is of an elastic material that is under tension at the time of attachment to the lower portion of the pad, its normally fully contracted length is shorter than that of the lower portion of the absorbent article. The elevated layer separates the soiled lower portion of the pad from the upper, desirably hydrophobic topsheet layer, minimizing the user's contact with wetness.

The centrally positioned opening is desirably sized to accommodate the portion of a user's body from which exudate flows, such as a woman's perineal region from which menses exudes. In an alternative embodiment, the centrally positioned opening is desirably sized to accommodate a user's immediate vaginal region only.

The lower, spaced-apart absorbent portion of the absorbent article can be seen through such centrally positioned opening in the first liquid permeable topsheet layer, with little or no intermediate layer visual interruption, thereby allowing the direct passage of liquid/fluid from the user's body to the subjacent internal portions of an absorbent article. That is, any intermediate layer that may be directly bonded to the underside of the liquid permeable first topsheet layer along its length, does not block the visualization of the lower layer through the centrally positioned opening, and does not interfere with the flow of liquid through the opening. Further, any optional intermediate layer that is directly bonded along the garment-facing side of the first topsheet layer desirably includes a similarly sized and shaped macro-opening that is aligned with the macro-opening(s) of the first topsheet layer in the article depth direction.

The relaxed length of the upper liquid permeable topsheet layer (first topsheet) is always shorter than that of the lower liquid permeable second topsheet layer (lower portion of the absorbent article). The lower topsheet layer is desirably in one embodiment, hydrophilic so as to be more receptive to moisture that may be exuded onto the pad, such as through the first topsheet layer central or end openings.

The elevated, skin-contacting topsheet layer (upper, first topsheet layer) is desirably elastic so as to allow for the stretch and retraction of the layer as the user and the user's undergarment moves, maintaining close association of the upper topsheet layer with a user's body during daily activity, and without rupturing such layer over prolonged use. The spatial gap between the first liquid permeable, upper topsheet layer and the second liquid permeable lower topsheet layer during article use, keeps moisture from passing back through from the absorbent core layer(s) to the upper elevated, user-facing skin-contacting layer. This predictable spatial gap or void space between the topsheet layers, occurs at some time during article use (use being the time after an article is unfolded and placed in a user's undergarment). For example, such spatial gap can occur when the user is in a side, prone, or fetal sleeping position, or when the user is walking about.

Desirably in one embodiment, the void space is formed between the two topsheet layers along substantially the full length of the upper topsheet layer. By substantially, is meant at least 50% of the first topsheet layer length (which can in some instances be 50% of the overall article cupped length), but desirably at least 80% of the first topsheet layer length or alternatively, at least 90% of the first topsheet layer length along the article longitudinal direction.

Ventilation openings may be positioned along the article opposing lateral side edges, along the article opposing longitudinal ends or in both locations. Further, such ventilation end openings may be present in locations along the first topsheet user-facing surface such that the elevated, skin-contacting topsheet layer is attached to the lower portion of the absorbent article at least at four separated attachment zones, with ventilation openings situated between pairs of attachment zones at or adjacent each of the article opposing longitudinal direction ends. In such embodiments, the elevated, skin-contacting topsheet layer (first liquid permeable topsheet layer) partially defines the longitudinal direction end openings by its attachment zone configuration. Alternatively, such end openings may be defined entirely within the elevated, skin-contacting topsheet layer, towards the longitudinal ends (that is, surrounded on all sides by portions of the elevated, skin-contacting topsheet layer).

As noted, such elevated, skin-contacting layer is in one embodiment, desirably formed from a hydrophobic or semi-hydrophobic material (as opposed to a liquid impermeable material), so as to enhance the dryness sensation during use, but which still allows for liquid to permeate to a lower absorbent layer. The liquid may pass to lower layers of the absorbent article directly through the centrally positioned opening, directly through the end openings, or through the layer material itself. The term semi-hydrophobic is meant to include a combination of both hydrophilic and hydrophobic materials.

As noted, such stretchable, and desirably elastic, skin-contacting topsheet layer also conforms to a user's body so as to allow for eventual absorption by lower layers or capture of body exudates, despite movement of undergarments during daily activities. As the underlying layers might move with the user's underwear, the upper topsheet layer can remain in direct contact with the user's body as a result of its stretchable functionality.

In this fashion, an absorbent article is produced which reduces wetness and rewet sensations during use, by maintaining a predictable spatial gap between a first, elevated topsheet layer and second, spaced apart lower topsheet layer. By being predisposed to separate from lower absorbent article portions, such first topsheet layer discourages continuous direct contact of the user's skin/body with the soiled zone of the absorbent article, at least in the area of the article that is most likely to be located under the part of the user's body from which exudate flows. By discouraging continuous direct contact of the first topsheet layer with a storage component, propensity for rewet sensations is reduced. Such three-dimensional structure further allows for air circulation throughout the article so as to maintain dryness. By optionally providing additional lateral edge barriers either beneath the first topsheet layer, or between the first and second topsheet layers (while still maintaining void space between topsheet layers), enhanced protection from lateral leakage may also be provided by the article.

Figure 3:
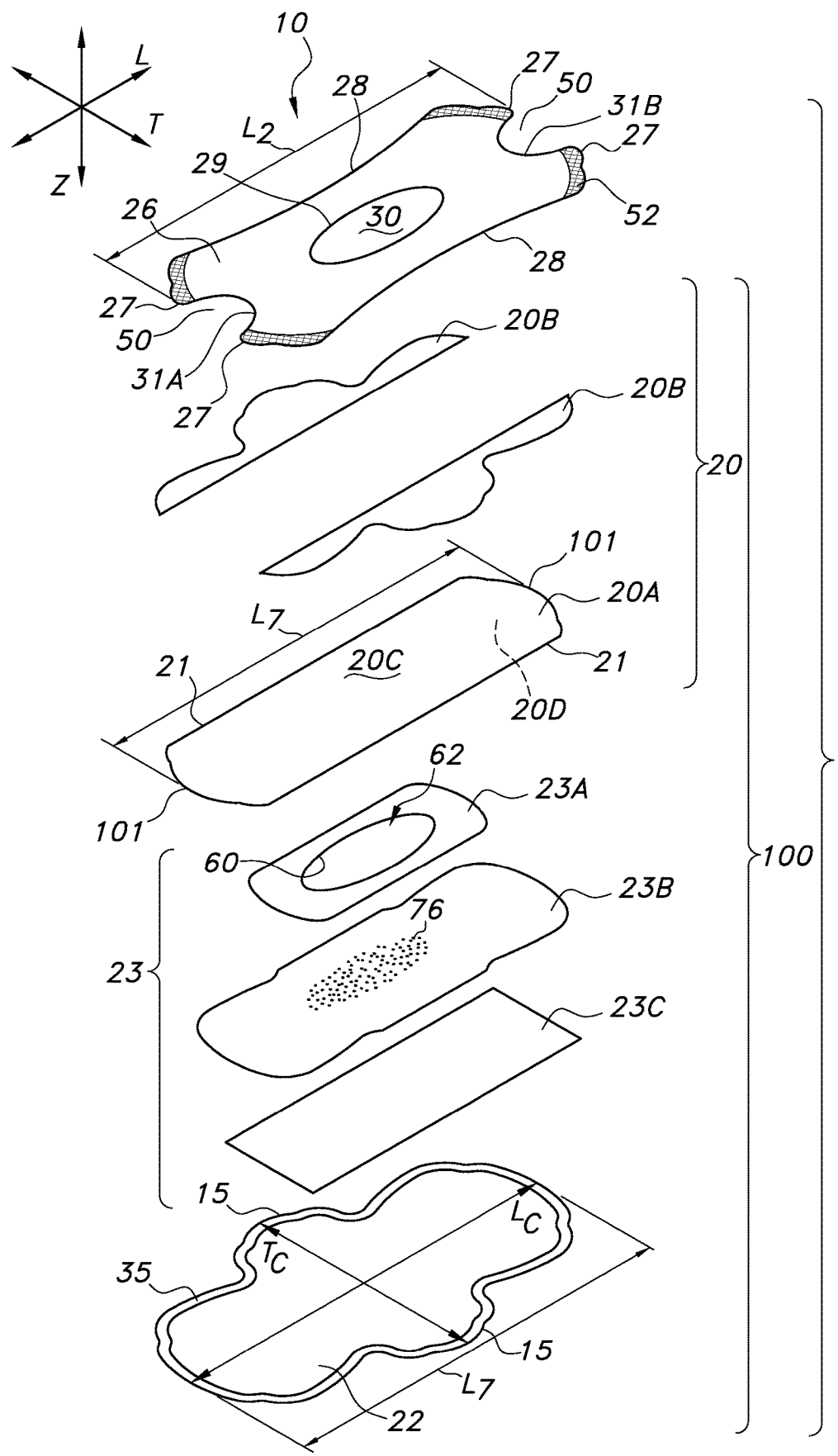
FIG. 3 illustrates an exploded, perspective view of the sanitary pad of FIG. 1.
Figure 5:
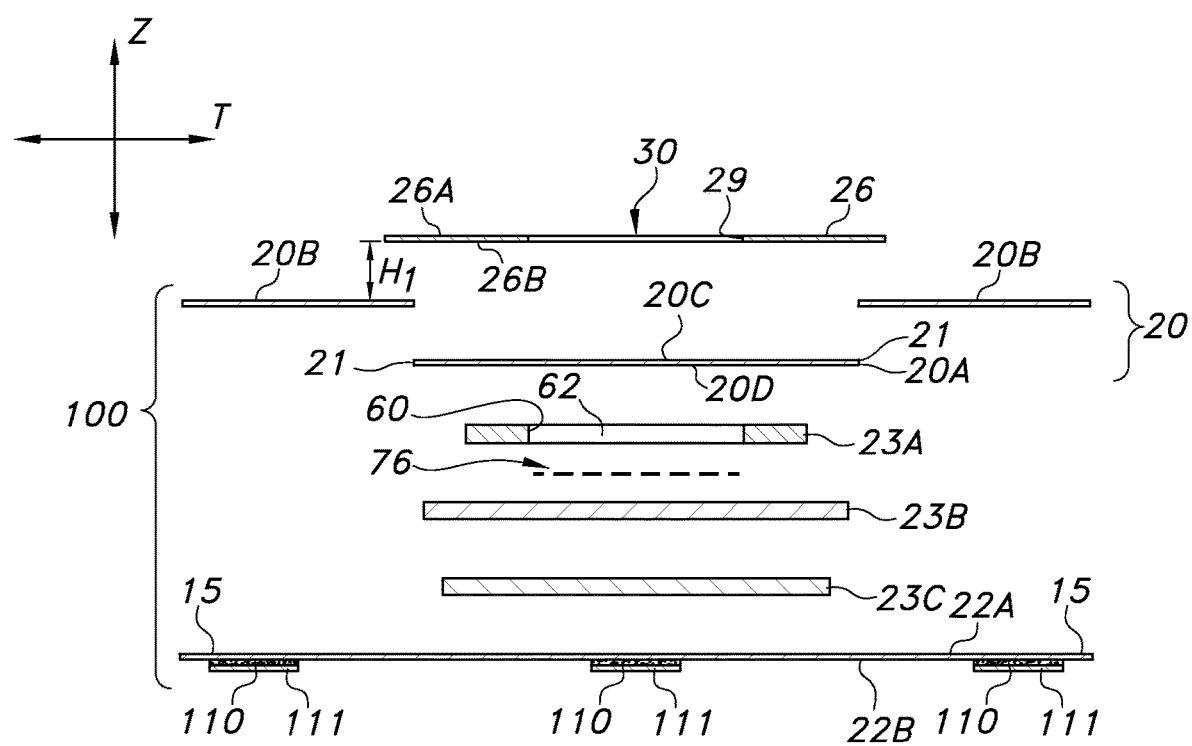
FIG. 5 illustrates an exploded cross-sectional view taken along line 5-5 of the pad of FIG. 1.

With reference specifically now to FIGS. 1, 3, and 5 respectively, a top plan view, an exploded perspective view, and an exploded cross-sectional view of an absorbent personal care article 10 in accordance with the invention is shown. The absorbent personal care article is in the form of a feminine hygiene sanitary pad 10. While a sanitary pad is illustrated in each of the figures for simplicity sake, it should be understood that a variety of absorbent articles can take advantage of the invention of the present disclosure.

The absorbent article (or pad as the case may be) 10 includes a longitudinal direction L, a transverse direction T, and a depth direction Z. The absorbent article also includes a central longitudinal direction Lc which separates the article into two symmetrical, longitudinally directed halves, and may include a central transverse direction Tc, which separates the article into two symmetrical halves as well (at least in the pad shown in FIG. 3). If the pad were of an asymmetrical shape, such as the shapes commonly found in overnight pad products (not shown), then a central transverse direction may not be possible. The absorbent article 10 includes opposing first and second longitudinal direction ends 11, 12 and opposing lateral side edges 13, 14 which extend between the absorbent article opposing first and second longitudinal direction ends 11, 12.

The absorbent article 10 includes a liquid permeable first topsheet layer 26, having a user-facing, skin-contacting surface 26A, and a garment-facing surface 26B (as seen in FIG. 5). The liquid permeable first topsheet layer is in one embodiment, entirely a planar sheet, as opposed to a combination of different construction materials, and serves as the upper topsheet layer in the article. Such desirably soft, planar sheet provides for enhanced comfort to a user, as opposed to a structure which includes different textures provided by ribbons, strings, or yarns in combination with a planar sheet. The liquid permeable first topsheet layer 26 is essentially an elevated, skin-contacting layer that at some period during article use, is elevated or seems to "float" above the lower portion 100 (FIG. 5) of the absorbent article, and is physically separated therefrom along a portion or substantially all of its length along the article longitudinal direction. By "substantially" is meant in a first embodiment, at least 50% of its length, alternatively, at least 80% of its length, still in a further embodiment, at least ninety 90% of its length is separated at some point in time, by a spatial gap from the absorbent article lower portion 100 (and the lower liquid permeable second topsheet layer 20).

In one embodiment, such liquid permeable first topsheet layer 26 is bonded to the liquid permeable second topsheet layer 20 (lower topsheet layer in the article depth direction Z) at, or adjacent the liquid permeable first topsheet layer opposing longitudinal direction ends 27, such that at least ninety 90% of its garment-facing surface 26B is not bonded to the subjacent liquid permeable second topsheet layer 20 user-facing surface; alternatively such that at least 80% of its garment-facing surface 26B is not bonded to the subjacent second topsheet layer user-facing surface. Alternatively (not shown), such liquid permeable first topsheet layer 26 may be bonded at its opposing longitudinal direction ends 27, to another layer within the lower portion 100 of the absorbent article, such as to the liquid impermeable backsheet layer 22 rather than the second topsheet layer. In such a situation, the second topsheet layer would be shorter in length than the backsheet layer. Desirably in one embodiment, there are no further bonds connecting the two topsheet layers along the first topsheet length, other than at the above described end bonds. In such an embodiment, only the end bonds/attachments hold the first and second topsheet layers to one another.

In its elevated state at some time period during article use, the distance of greatest separation of the liquid permeable first topsheet layer 26 from the lower portion 100 of the absorbent article (and the liquid permeable second topsheet layer thereon), can be measured as a height H1 (FIGS. 2A, 5). The distance of greatest separation H1, is often at a location adjacent the central insult region of the pad 10 (along the intersection of the central longitudinal direction and central transverse direction of the pad), and/or often adjacent the article wings 15 if present. The separation distance (that is the height of the void space between topsheet layers) can be fairly constant along large portions of the topsheet layer lengths, or may decrease from the central insult region to each of the article opposing longitudinal ends where it approaches no distance of separation (and consequently no void space). Such separation distance depends in part on the presence of, and the lengths of, the attachment zones 52 holding the topsheet layers (or first topsheet layer and other layer) together, the extensibility or elasticity of the first topsheet layer, and a user's compression of the pad. In one embodiment, the height H1 is between about, 0.0 mm and 30 mm, alternatively, between about 0.05 mm and 30 mm, alternatively, between about 0.1 mm and 20 mm, alternatively, between about 0.0 mm and about 6 mm, alternatively, between about 0.1 mm and 6 mm. Still in a further embodiment, the height H1 is between about 0.05 mm and 30 mm when the absorbent article is in a relaxed (and opened) condition. During use of the article, the distance of separation H may vary along the longitudinal direction L of the absorbent article 10 depending on the activities of the user. For example, when a user is in a sitting position, the distance of separation (space) may be eliminated. When a user is in a sleeping or walking position, the distance of separation may approach its maximum possible values. The ability of the separation distance to continually reach its maximum possible value over prolonged article use, will also be dependent on the elastic properties of the first topsheet layer and bond strength between the first and second topsheet layers (or other layers within the lower portion of the pad).

Figure 2D:
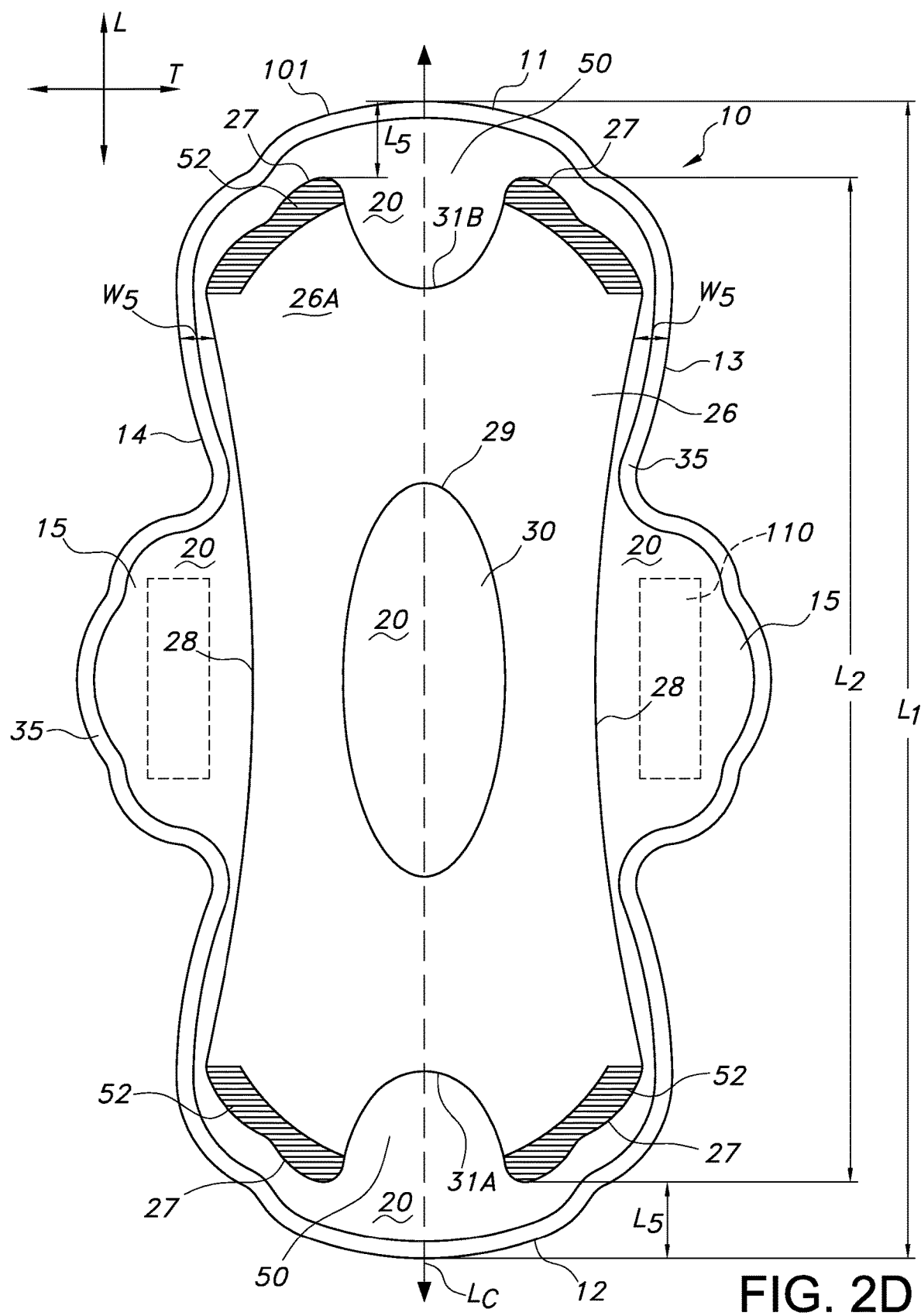
FIG. 2D illustrates a top plan view of a different embodiment of a sanitary pad with an elevated skin-contacting, first topsheet layer of relatively shorter dimensions than prior embodiments, attached inwardly of the absorbent article opposing longitudinal ends.

As noted, the planar, liquid permeable first topsheet layer 26 includes first topsheet layer opposing longitudinal direction ends 27 and first topsheet layer opposing lateral side edges 28 extending between the first topsheet layer opposing longitudinal direction ends 27. In one embodiment following pad manufacture, the first topsheet layer opposing longitudinal direction ends extend 27 directly between the absorbent article opposing longitudinal direction ends 11, 12 (as seen in FIGS. 1, 3, and 5). In such an embodiment, the absorbent article takes on an upwardly-directed cupped configuration, that is, the absorbent article lower portion 100, takes on a curvature towards the liquid permeable first topsheet layer. In an alternative embodiment, following pad manufacture, the absorbent article opposing longitudinal direction ends 11,12 extend to a position outwardly beyond the opposing longitudinal direction ends 27 of the liquid permeable first topsheet layer 26, as seen in FIG. 2D. In such a configuration, the absorbent article also takes on an upwardly cupped configuration however. No matter the embodiment, the actual relaxed length of the liquid permeable first topsheet layer 26 along the longitudinal direction (in a relaxed, flattened state, and prior to article construction) will always be shorter than that of the relaxed lower portion 100 of the absorbent article 10, and desirably also the relaxed length of the liquid permeable second topsheet layer 20 as well. As a result of this difference in layer/article starting lengths, with the absorbent article in a relaxed position (without compression and opened on a flat surface such that the liquid permeable first topsheet layer faces upward), the liquid permeable first topsheet layer holds the article in the curved or cupped configuration while in a relaxed state. That is, at least the absorbent article lower portion 100 or the entire article will take on a curved configuration along the longitudinal direction, with the liquid permeable first topsheet layer 26 either being relatively level with respect to the lower portion 100, or itself being curved upward as well. In a relaxed open state, such article is maintained in such curved configuration by the liquid permeable first topsheet layer 26.

Such liquid permeable first topsheet layer 26 is stretchable or extensible at least along the absorbent article longitudinal direction. In a further embodiment, such liquid permeable first topsheet layer 26 is elastic at least along the absorbent article longitudinal direction. In yet a further embodiment, such liquid permeable first topsheet layer 26 is in a pretensioned state (and elastic) at least along the absorbent article longitudinal direction, either prior to, or while it is attached to the absorbent article lower portion 100 (or liquid permeable second topsheet layer 20) such that it takes on an accentuated curved shape following attachment. In such an embodiment, its fully retracted (relaxed) length is shorter than that of the lower portion 100 of the absorbent article. In such an embodiment, the liquid permeable first topsheet layer 26 may be stretched from between about 2 and 18 percent its length, alternatively between about 3 and 12 percent its length, alternatively between about 3 and 8 percent its length prior to attachment to the absorbent article lower portion 100 (or the liquid permeable second topsheet layer 20). Following attachment, the retraction of the elastic layer will cause the curved condition of the overall absorbent article. Such pre-attachment, stretched distance can in one embodiment be equal to the length difference between the relaxed absorbent article lower portion 100 (and second topsheet layer) length L7, and the relaxed liquid permeable first topsheet layer length L2 (as seen in FIG. 3). The relaxed absorbent article lower portion 100 length L7 is always longer than the relaxed liquid permeable first topsheet layer length L2. The relaxed second topsheet layer length is desirably in one embodiment, also longer than the relaxed first tosphheet layer length L2 (as in one embodiment, the second topsheet layer length is the same as the backsheet layer length).

In still another alternative embodiment (not shown), such liquid permeable first topsheet layer 26 may include alternating elastic and inelastic portions of material running in continuous strips across the absorbent article transverse direction (the strips alternating between elastic and inelastic along the length of the layer), such that the layer is ultimately elastic at least along the absorbent article longitudinal direction. Such inelastic portions may themselves be nonextensible or extensible. In yet still another alternative embodiment, the liquid permeable first topsheet layer 26 may be elastic, but not bonded to the liquid permeable second tophsheet layer 20 while in a pre-tensioned state.

Figure 2E:
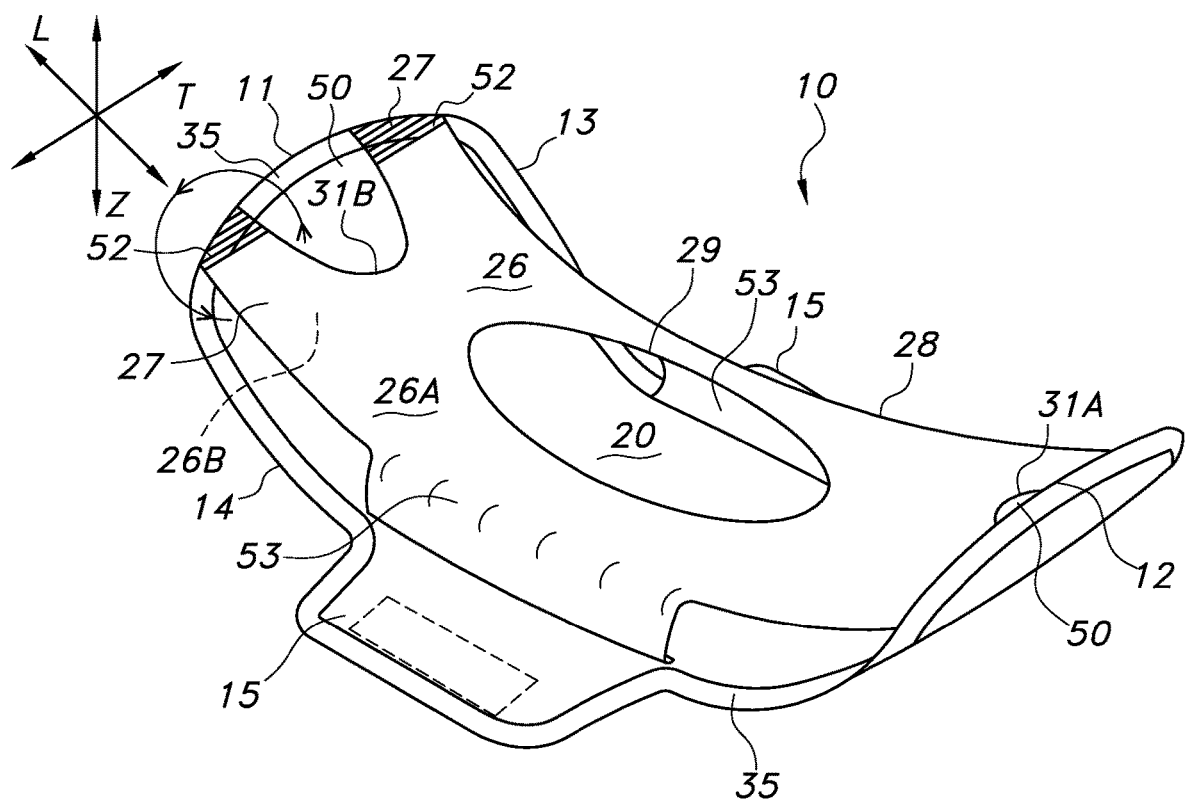
FIG. 2E illustrates a top perspective view of a different embodiment of a sanitary pad with wings positioned outwardly from the opposing lateral side edges, and including limited topsheet layer attachments along the absorbent article opposing lateral side edges

The stretch properties of the liquid permeable first topsheet layer 26 may be varied as desired in order to achieve desired levels of conformity to a user's body during prolonged use, and to achieve a desired separation distance between topsheet layers. However, in one embodiment, the load at three (3) percent extension of the liquid permeable first topsheet layer 26 along the absorbent article longitudinal direction, is desirably between 20 and 200 gf. In a second embodiment, the load at five (5) percent extension of the liquid permeable first topsheet layer 26 along the absorbent article longitudinal direction, is desirably between about 50 and 350 gf. In yet another embodiment, the load at eight (8) percent extension of the liquid permeable first topsheet layer 26 along the absorbent article longitudinal direction, is desirably between about 80 and 450 gf. Finally, in still yet another alternative embodiment, the load at twelve (12) percent extension of the liquid permeable first topsheet layer 26 along the absorbent article longitudinal direction, is desirably between about 100 and 600 gf. If the material of the first topsheet layer is elastic but not bonded to the second topsheet layer in a tensioned condition at the time of attachment, the first topsheet layer is less likely to curl upon itself at the article opposing longitudinal direction ends 11, 12. If it is to be bonded to the second topsheet layer when in a tensioned condition, it is desirable that the retractive force of the first topsheet layer should not be so much stronger than the resisting force of the second topsheet layer (or lower portion of the absorbent article) so as to cause curling of the absorbent article ends such that they extend over the first topsheet layer. As seen in FIGS. 2-2E, and especially in FIG. 2, such article opposing longitudinal direction ends 11, 12 all curve outwardly, but not in a configuration in which the first topsheet layer 26 extends back over itself.

In one embodiment, the distance between the first topsheet layer opposing lateral side edges 28 is desirably shorter along the absorbent article transverse direction (as seen in FIG. 1) than the distance between the overall absorbent article opposing lateral side edges 13, 14. In an alternative embodiment, the distance between the first topsheet layer opposing lateral side edges 28 along the transverse direction may be approximately the same as that between the overall absorbent article opposing lateral side edges 13, 14.

The liquid permeable first topsheet layer 26 is attached to the lower portion 100 of the absorbent article (essentially to a subjacent layer in the absorbent article depth direction, desirably, the liquid permeable second topsheet layer 20), at the liquid permeable second topsheet layer user-facing side, at attachment zones 52. After attachment of the liquid permeable first topsheet layer 26 to the liquid permeable second topsheet layer 20, the absorbent article takes on the curved configuration (as seen in FIGS. 2A-2C), such that a concavity extends at least along the lower portion 100 of the absorbent article along the longitudinal direction L, when the absorbent article itself is in an opened and relaxed condition. This concavity is a result at least of the liquid permeable first topsheet layer 26 being always of shorter relaxed length than the overall relaxed absorbent article lower portion 100 length.

The spatial gap formed between the two topsheet layers is present prior to folding of the absorbent article 10 for storage if such is the case, or alternatively, during absorbent article storage. If folded, this spatial gap may be temporarily eliminated if the liquid permeable first topsheet layer 26 is elastic. If folded for storage, upon unfolding of the absorbent article 10, this spatial gap should re-form along the length of the absorbent article, at least when the product is in a relaxed state as seen in FIGS. 2-2C. If stored in a folded configuration, the manufacturing steps of folding and storage should not result in the permanent deformation of the liquid permeable first topsheet layer 26 such that its relaxed length dimension upon unfolding, is the same as the relaxed length of the lower portion 100 of the absorbent article 10. Essentially its relaxed length should never be equal after unfolding, to the relaxed length dimension of the article lower portion 100, and desirably also, the relaxed length of the liquid permeable second topsheet layer 20 and the backsheet layer 22. If such were the case, the liquid permeable first topsheet layer 26 would merely lay flat (with no distance of separation during use) on the liquid permeable second topsheet layer 20 along the full length of the overlap, and not rise above it, resulting in continuous contact with a lower absorbent portion of the article. The acts of folding and storage should therefore not result in the liquid permeable first topsheet layer 26 permanently maintaining its ultimate elongation/extension prior to use.

A demonstrated attribute of the absorbent article 10 upon removal from a storage container or following unfolding, should be further available elongation of the liquid permeable first topsheet layer 26, during absorbent article use in a user's undergarment. Such further available elongation can be the result of its elasticity properties, if it is manufactured from an elastic material. Such absorbent article may be folded along its central longitudinal direction rather than at one or more transverse directional fold lines, so as to avoid unnecessary permanent deformation of the liquid permeable first topsheet layer 26 along the absorbent article longitudinal direction.

As noted, the liquid permeable first topsheet layer is extensible (and desirably elastic) in at least the absorbent article longitudinal direction. The ability of the liquid permeable first topsheet layer 26 to extend may be the result of either the inherent polymeric properties of the materials from which the layer is manufactured, from mechanical treatment of the materials from which it is made, or alternatively, result from macro-structures which make up the layer 26. For example, the layer 26 may be manufactured from fibrous or woven strand/ribbon materials which allow for extensibility, as such fibers or woven strands slide past one another in the structure upon layer extension. Alternatively, the layer may extend as a result of deformation of the polymeric material from which it is made. Alternatively, the layer 26 may be subjected to layer 26 post-formation processing, such as by being exposed to incremental stretching (as through pairs of grooved or interdigitating rolls such as those well known in the art), or by being given extendable three-dimensional surface topographies (as described for example, as SELF materials in U.S. Pat. No. 5,554,143 to Roe et al., which is incorporated herein in its entirety by reference thereto). Each of these processes or a combination thereof will allow for the liquid permeable first topsheet layer 26 to extend to a certain extent without rupture. Of course, the liquid permeable first topsheet layer 26 is desirably formed from truly elastic materials (of a single layer) or elastic laminate materials (of a greater number of layers than a single layer), each of which will provide greater flexibility in absorbent article design and comfort for a user.

The first topsheet layer opposing longitudinal direction ends 27 may number at least two, but can be higher in number, such as comprising the four discrete lobes 27 making up the opposing longitudinal ends that are shown in the figures. The first topsheet layer opposing longitudinal direction ends 27 desirably include four lobes, with two of each lobes 27 positioned at or adjacent each absorbent article longitudinal direction end 11, 12. The ends (or lobes) 27 are desirably in one embodiment, separated by a space, or ventilation end opening 50 between lobes 27, which end opening desirably is defined by a curvilinear recess edge 31A, 31B. At the recess edges 31A, 31B such liquid permeable first topsheet layer 26 is desirably not entirely bonded in the depth direction to the lower portion 100 of the absorbent article or any subjacent layer. For example as seen in FIG. 1, attachment zones 52, which bond the first topsheet layer to the second topsheet layer, extend partially along the absorbent article peripheral edge within the absorbent article peripheral seal area 35, and partially along the recess edges 31A, 31B. The peripheral seal area 35 also seals various layers of the absorbent article lower portion 100 together. For example, such peripheral seal area 35 seals the liquid permeable second topsheet layer 20, the optional liquid handling/transfer/surge layers, the one or more absorbent core layers 23, and the liquid impermeable backsheet layer 22 together.

In FIG. 2, the attachment zones 52 (shown as parallel stripes) extend partially along the recess edges 31A, 31B of the ventilation end openings 50, but not entirely around the end openings 50. In FIG. 2A, the attachment zones 52 extend along larger portions of the recess edges 31A, 31B defining the ventilation end openings 50. The attachment zones 52 do not encompass such spaces 50, that is, there is an unbonded area between adjacent attachment zones 52 along the article transverse direction, in which the liquid permeable first topsheet layer 26 is not bonded to a subjacent layer (such as the liquid permeable second topsheet layer 20). That portion of the liquid permeable first topsheet layer 26 extending between opposing longitudinal direction ends 27, (as opposed to between adjacent lobes), may either be level or curved along the absorbent article length L.

As illustrated, such recess edges in the liquid permeable first topsheet layer 31A, 31B are desirably semicircular in configuration, but may alternatively be of a variety of geometric or abstract shapes, such as ovular, U-shaped or rectangular for example. While shown as being a partial recess (in that the end openings 50 are not completely surrounded by portions of each end of the liquid permeable first topsheet layer 26), such recess edges 31A, 31B defining the shapes of the end openings 50, may in an alternative embodiment (not shown), completely encircle a ventilation end opening 50 such that the end opening is entirely contained within, and enclosed by portions of the liquid permeable first topsheet layer 26. Such recess edges 31A and 31B, (and consequently, formed end openings 50), may be of the same shape or of different shapes at each opposing longitudinal direction end 11, 12 of the absorbent article. Desirably, such are of the same shape at each absorbent article opposing longitudinal direction end 11, 12, and are aligned along the central longitudinal direction Lc of the absorbent article 10. While two such end openings 50 are shown, it should be recognized that multiple end openings 50 may instead be present at or adjacent the first topsheet layer 26 opposing longitudinal direction ends 27, defined by multiple lobes or end pieces.

It should be recognized that in one desirable embodiment, the attachment zones 52 do not extend completely along the recess edges 31A, 31B. In those embodiments in which the attachment zones 52 do extend completely along the recess edges 31A, 31B, the end openings 50 exist but are not elevated with a significant spatial void between the topsheet layers. Rather, in such an embodiment, the second topsheet layer is situated immediately beneath the end openings, without a gap.

Desirably in one embodiment, the opposing longitudinal ends 27 of the liquid permeable first topsheet layer 26 (or lobes as seen in FIG. 1) are shaped similarly to the absorbent article opposing longitudinal direction ends 11, 12, or at least portions thereof. For example, as seen in FIG. 1, the opposing longitudinal direction ends of the pad 11, 12 and first topsheet layer 27 ends include multiple, scalloped-shaped peripheral edges. Alternatively, the peripheral edges of such first topsheet layer ends 27 may merely match a simple, curved peripheral edge shape of the absorbent article opposing longitudinal direction ends 11, 12, as seen in FIG. 2A.

The liquid permeable first topsheet layer 26 further defines, by an interiorly situated edge 29, a macro-opening 30 to facilitate direct passage of liquid/fluid through the liquid permeable first topsheet layer 26 to the lower portion 100 (and layer 20) of the absorbent article 10, along the absorbent article depth direction Z. The opening 30 is desirably in one embodiment, centrally located within the pad, and allows the uninterrupted passage of exudate liquid/fluid from a user, to the interior liquid handling and absorbent core layers (storage components) (23A-C) of the absorbent article 10. The opening 30 is large enough to allow the unimpeded viewing of the lower layers of the absorbent article 10 (at least the liquid permeable second topsheet layer 20) through the opening 30, and may consist of a single opening as shown (in oval shape for example) or multiple proximate openings of the same or various shapes. The opening is desirably a single, relatively large opening that is centrally located, such that it is situated along both the central longitudinal direction Lc and the central transverse direction Tc (if present), in a central insult region of the absorbent article. The opening is also desirably situated adjacent and/or between wing features 15, if such are present. The central opening 30, may be of a variety of shapes, such as a symmetrical geometric or asymmetrical abstract shape. Specific examples of such opening shapes include circular, oval, elliptical, rectangular, and oblong. Opening shapes with curvilinear features are desirable. In one embodiment, such central opening is sized to fit about the perineal region of the female anatomy, desirably closely about the female vagina. In an alternative embodiment (not shown), such central opening 30 is positioned between adjacent wing features 15, but such wing features 15 and central opening 30 are placed closer to one longitudinal end of the pad 10 than the other. Such may be desirable for traditionally asymmetric and extended length, overnight pads for example.

As further seen in FIG. 1, printed or other visually apparent features 76 of the absorbent article lower portion 100 can be seen through the opening 30. Such printed features may include a series of printed or embossed dots or geometric shapes. Desirably in one embodiment, the visually apparent features 76 are isolated to a design configuration and location on a subjacent layer, that is aligned with the shape of the opening 30. That is, if the opening is of an oval shape, it is desirable in one embodiment for the visually apparent features to be present in a generally oval shape, such as on surface area of the subjacent layer equal to that of the central opening 30 and aligned with it. Such visually apparent features act to highlight the presence of the opening. In an alternative embodiment, such visually apparent features 76 may only be seen though said opening 30 but actually extend on the printed or otherwise marked subjacent layer beyond the lateral and longitudinal boundaries of the opening shape above it.

Desirably in one embodiment, the opening 30 is positioned along the central longitudinal direction Lc of the absorbent article 10, and is aligned with the end openings 50 of each first topsheet layer opposing longitudinal direction end 27. In an alternative embodiment, the shapes of the openings 30, 50 may be similar or include similar elements. For example, the end openings 50 may be semicircular or semi-oval, and the central opening 30 may be circular or oval. Alternatively, all three openings may be circular or oval.

The liquid permeable first topsheet layer 26 is desirably liquid permeable along its entire dimensions (aside from the obvious permeability through its central opening 30 and end openings 50). The layer is desirably in one embodiment, hydrophobic or semi-hydrophobic, so as to maintain a feeling of dryness. The liquid permeable first topsheet layer 26 may be manufactured from a single layer or a laminate of layers, as long as such layers do not include a storage component; as long as such layers do not interfere with the direct flow of liquid to the lower portion of the article 100; and as long as such additional layers do not interfere with the visualization of the absorbent article lower portion 100 (and liquid permeable second topsheet layer 20) through the liquid permeable first topsheet layer central opening. In a further embodiment, such optional additional layer should also not interfere with the visualization of the lower portion 100 through the end openings as well. Desirably in one embodiment, any optional/additional layers directly bonded to the garment-facing surface 26B of the liquid permeable first topsheet layer 26 include openings that are aligned in shape and/or size with the openings in the liquid permeable first topsheet layer 26 along the article depth direction Z.

As noted, the absorbent article 10 further includes a spaced apart liquid permeable second topsheet layer 20 subjacent to and at times, spaced apart from the liquid permeable first topsheet layer 26. Such second topsheet layer desirably includes at least a hydrophilic portion, and alternatively is entirely hydrophilic. Since the liquid permeable first topsheet layer may be the same width or narrower than the liquid permeable second topsheet layer, the liquid permeable first topsheet layer overlaps at least a portion of the liquid permeable second topsheet layer in the absorbent article depth direction Z. The liquid permeable second topsheet layer 20 may be manufactured of a single layer (FIGS. 2-2D), or alternatively of multiple, side-by-side layers of material (FIGS. 1, 3, 5). In either case, it is desirable in one embodiment, that the planar liquid permeable second topsheet layer 20 extends fully to the absorbent article opposing longitudinal direction ends 11, 12 and the absorbent article opposing lateral side edges 13, 14, being also bonded to the subjacent liquid impermeable backsheet layer 22.

If present, a side-by-side, liquid permeable second topsheet layer 20 includes a central, longitudinally directed topsheet material layer 20A (central topsheet section), and two side topsheet material layers 20B (side topsheet sections) which straddle the lateral side edges 21 of the central, longitudinally directed topsheet material layer 20A. As with the other layers in the article, the central, longitudinally directed topsheet material layer 20A includes a user-facing surface 20C and a garment-facing surface 20D, and the side topsheet layer materials 20B may be bonded to the central, longitudinally directed topsheet material layer 20A at either the user-facing surface 20C or the garment-facing surface 20D. The central, longitudinally directed topsheet layer 20A may traverse the full width of the absorbent article 10, or only a portion of the width along the absorbent article transverse direction T as seen in FIG. 5. However, the totality of multiple layer widths of a liquid permeable second topsheet layer 20 (in such an embodiment) desirably extend the full width of the absorbent article 10, such as over the wings 15 as well. The lateral side edges 21 (of the central longitudinally directed topsheet material layer 20A) are desirably bonded to the two side topsheet material layers 20B by a line of adhesive (not shown) along the longitudinal direction L of the absorbent article 10.

Such liquid permeable second topsheet layer 20 (in either the single or multiple layer format) may include on its surface (either by itself or including the rest of the absorbent article lower portion 100), one or more embossment features 75 for either aesthetic of functional purposes. Such embossments may be designed for the purposes of impacting article bending preferences while in use, to further direct liquid flow, or for purely aesthetic ornamentation. While, the illustrated embossment feature 75 includes a scalloped, racetrack-like pattern and separate arcs, any discrete functional channel(s) or ornamental patterns may be employed as are well known in the embossment art. Such embossments are typically created by pressure and/or thermal bonding techniques, and may themselves include smaller embossment features within the channels of larger embossment features. A cross-hatching, microembossment design is illustrated in the figures, for example.

The liquid permeable second topsheet layer 20 includes opposing longitudinal direction ends 101 that may be the same shape as the opposing longitudinal direction ends 27 of the liquid permeable first topsheet layer 26 or of different shape. Desirably, in one embodiment, the peripheral edge shape (as opposed to size) of the liquid permeable first and second topsheet layers, and backsheet layer 22, are similar or the same, at least in portions.

As noted previously, in use (not in a folded condition), the absorbent article 10 includes a void space between the liquid permeable first topsheet layer 26 and the liquid permeable second topsheet layer 20, separated by a distance. The liquid permeable first topsheet layer 26 (upper topsheet layer in the Z direction) is bonded or otherwise attached to the liquid permeable second topsheet layer 20 (lower topsheet layer in the Z direction) by multiple attachment zones 52 at or adjacent its longitudinal ends. Such multiple attachment zones may correspond in number to the number of ends/lobes 27 of the liquid permeable first topsheet layer 26, but need not. For example, as shown in FIGS. 1, 2, and 2D, such attachment zones 52 desirably number four, one for each lobe 27. Such attachment zones may be created by discrete areas of adhesive 95 between subjacent layers in the Z direction (in FIG. 4), thermal, pressure, or other bonding techniques (or combination of techniques). Such attachment zones 52 limit attachment of the liquid permeable first topsheet layer 26 and subjacent layers to discrete areas only on the liquid permeable first topsheet layer, at or adjacent the opposing longitudinal direction ends 27 of the first topsheet layer, which may also be at or adjacent the opposing longitudinal direction ends 11,12 of the absorbent article. Such attachment zones 52 are desirably situated at or adjacent the opposing longitudinal direction ends 101 of the liquid permeable second topsheet layer 20. They 52 may be completely separated from one another, or may continue into one another as seen in FIG. 2A.

As noted, the attachment zones 52 may be desirably placed within the peripheral seal regions 35 only (FIG. 1), of the absorbent article, or may be comprised of their own discrete narrow zones separated from the peripheral seal regions 35, as seen in FIG. 2D for example. When the attachment zones 52 are placed within the peripheral seal regions 35, they may include different attachment mechanisms (such as adhesive) than those which seal the overall article in the seal region (thermal or ultrasonic for example), or they may be comprised of the same sealing mechanisms. For example, the peripheral seal 35 may accomplish both the sealing of the overall article as well as the attachment of the first topsheet layer 26 to the second topsheet layer 20. By including discrete attachment zones 52 at the liquid permeable first topsheet layer longitudinal direction ends 27 separated by spaces 50, the remaining unbonded areas of the liquid permeable first topsheet layer 26 are allowed in some embodiments, to elevate or float above the underlying layers during use. The smaller the attachment zone 52 (and the farther the zone is from the end opening recess edges), the more the end openings 50 are permitted to open fully and the surrounding liquid permeable first topsheet layer 26 is permitted to float above the lower portion of the absorbent article (and liquid permeable second topsheet layer 20) at the longitudinal ends. These openings essentially create additional ventilation opportunities for air to circulate between the lobes 27, across the topsheet layers and through the pad. For example, as seen in FIG. 2, ventilation openings are present along the opposing lateral side edges 13, 14 of the absorbent article, and at the opposing longitudinal direction ends 11, 12 of the absorbent article. In embodiments (not shown) in which the absorbent article opposing longitudinal direction ends 11, 12 do not include end openings 50, ventilation occurs along the absorbent article opposing lateral side edges 13,14. Ventilation is enhanced by an increased number of openings along all sides/ends of the absorbent article, although increasing the number of openings to a very large number may impact the ability of the liquid permeable first topsheet layer 26 to withstand compression without rupturing during use, as a result of compromised strength from multiple narrow attachment zones. As can be seen, the ventilation may be accomplished by openings present along either the vertical side edges of the absorbent article, the upper user-facing surface at the longitudinal direction ends 27 of the liquid permeable first topsheet layer 26, or a combination of both. The stylized circulation of air across the opposing longitudinal direction ends 27 of the liquid permeable first topsheet layer 26 (and absorbent article ends 11, 12) is shown in FIGS. 2A and 2B by arrows in a circle at one end of the article.

The absorbent article desirably further includes a liquid impermeable backsheet layer 22 which is, together with the topsheet layers, sealed at the absorbent article peripheral edges 35 to sandwich one or more liquid control/transfer, or handling layers and absorbent core layers 23A, 23B, and 23C, within the absorbent article 10. As noted, printed or other visually apparent features 76 may be strategically positioned on either the liquid permeable second topsheet layer 20 (such as the underlying garment-facing surface), an underlying liquid control or transfer layer, or an absorbent core layer, such that they can be viewed through the centrally positioned opening 30 of the liquid permeable first topsheet layer 26. Such features may assist the user in placement of the article during use, by highlighting the article region to be placed under a user's perineal area. Although not shown in the figures, additional visually apparent features may be present on a layer or layers of the absorbent article lower portion 100 directly under central opening 30 or the end openings 50, so as to highlight the presence of such ventilation end openings.

While shown in FIG. 1 to include overlapping opposing longitudinal direction ends, the liquid permeable first and second topsheet layers 26, 20 may alternatively include ends which do not overlap at all or completely. For example in FIGS. 1, 2, and 2A, they overlap (having similar longitudinal end shapes/profiles), while in FIG. 2D, they are of similar profile shape at the ends, but do not overlap. As a result, the attachment zones 52 on the lobes 27 of the liquid permeable first topsheet layer 26 in FIG. 2D are positioned inwardly from the opposing longitudinal direction ends 11, 12 of the absorbent article 10 (and opposing longitudinal direction ends 101 of the underlying liquid permeable second topsheet layer 20). In such an embodiment, such floating layer extends across a shorter length of the absorbent article longitudinal direction.

Subjacent to the liquid permeable second topsheet layer 20 in the absorbent article Z direction, is located one or more liquid control/transfer, or handling layer and absorbent core layers 23A, 23B, 23C. Such layers are responsible for directing liquid flow through the Z direction of the absorbent article to a storage component within the absorbent article 10 (which in this case is layer 23C). As seen in FIGS. 1, 3, and 5, at least one of these liquid control/transfer layers may also include an interiorly positioned edge 60 that defines a layer with another centrally positioned aperture/opening 62. Such interiorly positioned edge 60 may be situated to be more centrally located than the liquid permeable first topsheet layer edge 29, such that the central opening 30 and centrally positioned aperture 62 are aligned with one another, desirably with one being slightly smaller than the other. The openings, if more than one are present, may be of the same shape and size, or of different shapes and sizes. By aligning the openings in the Z direction (and along the L and T directions), liquid can rapidly travel to and be absorbed directly into the storage component 23C of the absorbent article 10. The alignment of layer inner edges 29, 60 and macro-openings/apertures 30, 62 defined by such inner edges, in the depth direction, operates to create a funnel-like structure, which quickly directs liquid from a user to the storage component (absorbent core) of the article. Such funnel-like structure enhances the collection of liquid/fluid while maintaining a spatial gap between the user and the storage component, thereby reducing rewet and enhancing user comfort. Such lower layer may in one embodiment, operate to provide a raised, hump-like feature in the central region of the pad. In FIG. 5, the absorbent core layer is shown as being directly adjacent the liquid impermeable backsheet layer 22 such that absorbed liquid is retained within the absorbent article 10. It should be recognized that while only three layers 23A, 23B and 23C are illustrated in FIGS. 3 and 5 as being positioned between the liquid permeable second topsheet layer 20 and the liquid impermeable backsheet layer 22, additional liquid handling layers, such as surge layers, can also be immediately subjacent to the second topsheet layer 20.

The absorbent article 10 may optionally include outwardly directed wings or tabs 15 which extend from each of the opposing lateral side edges 13, 14 of the absorbent article 10. The wings 15 assist in the adherence of the absorbent article 10 to a user's undergarments by folding about the side edges of the crotch region of a user's undergarments (not shown) and attaching to either each other or the garment-facing side (not shown) of a user's undergarment. The wings 15 may be of integral construction with the absorbent article topsheet and backsheet layers 20, 22, or may, alternatively, be of non-integral construction, and separately applied at a later stage of absorbent article manufacture. In one embodiment such wings 15 are positioned along the central transverse direction Tc of the absorbent article (as seen in FIG. 3) so as to facilitate attachment of the absorbent article in the narrower crotch region of a user's undergarments only. While not shown in all of the various figures, it should be understood that various attachment or bonding mechanisms such as patches of garment adhesive 110, hook and loop fasteners, or other structures may be positioned on either the garment-facing surface of the backsheet layer 22 or the garment-facing surface of the wings (if present) so as to improve adherence of the absorbent article 10 to the user's undergarments. Such garment adhesive 110 patches are also desirably covered by removable release sheets 111 for protecting the adhesive patches 110 until use.

Desirably in one embodiment, the length L1 of the absorbent article of the invention in its cupped or curved configuration is between about 15 cm and 25 cm for regular-sized pads, but inclusive of overnight pads is between about 15 cm and about 50 cm, alternatively between about 17 cm and 22 cm for regular-sized pads, but inclusive of overnight pads is between about 17 cm and 45 cm. In the regular pad configuration as shown in FIG. 1, the cupped length L1 of the absorbent article 10 (length when in a cupped configuration), and the length L2 of the liquid permeable first topsheet layer 26 itself, may be the same. The cupped lengths of the liquid permeable second topsheet layer and backsheet layer are desirably similar or the same. In one embodiment, the actual relaxed lengths L7 (as seen in FIG. 3) of the liquid permeable second topsheet layer 20 and backsheet layer 22 (and/or absorbent article lower portion 100) are desirably between about 15 cm and 30 cm for regular-sized pads, but inclusive of overnight pads is between about 15 cm and 50 cm, alternatively between about 18 cm and 28 cm for regular-sized pads, but inclusive of overnight pads is between about 18 cm and 43 cm. Desirably in one embodiment, the actual relaxed length of the liquid permeable first topsheet layer L2 is between about 15 cm and 28 cm for regular-sized pads, but inclusive of overnight pads is between about 15 cm and 48 cm, alternatively between about 18 cm and 24 cm for regular-sized pads (which is in some embodiments equal to the cupped length of the absorbent article 10), but inclusive of overnight pads is between about 18 cm and 41 cm. For that embodiment shown in FIG. 2D for example, the cupped lengths of the absorbent article and first topsheet layer would differ. The selected length of the first topsheet layer L2 will in part, depend on the stretchability of the first topsheet layer. For example, if such layer is capable of stretching easily, then the length of such layer need not be similar to that of the lower portion 100 of the absorbent article (or second topsheet layer 20), and can be significant shorter than that of the lower portion of the absorbent article. Desirably, in one embodiment, the length L3 of the centrally positioned opening 30 is between about 5 cm and 20 cm, alternatively between about 6 cm and 15 cm. Desirably, in one embodiment the length L4 of the end openings 50 is between about 0.1 cm and 7 cm, alternatively between about 1 cm and 4.5 cm. Such length may also correspond to the length of the attachment zones 52. Desirably, if present, in one embodiment the topsheet layer end separation distance L5 between the longitudinal direction end 27 of the liquid permeable first topsheet layer 26 and longitudinal direction end 101 of the second topsheet layer 20 is between about 1 cm and 5.5 cm, alternatively between about 1 cm and 3 cm. Desirably in one embodiment, the width W1 of the absorbent article 10 is between about 8 cm and 25 cm, alternatively between about 12 cm and 18 cm (including wings if present). The width of the liquid permeable second topsheet layer 20 and backsheet layer 22 may also desirably correspond to this width range W1. Desirably, in one embodiment, the width W2 of the liquid permeable first topsheet layer 26 is between about 6 cm and 15 cm, alternatively between about 7.5 cm and 12 cm. Desirably, in one embodiment, the width W3 of the central opening 30 is between about 1 cm and 5 cm, alternatively between about 2 cm and 3.5 cm. Desirably, in one embodiment the width W4 of the end opening 50 is between about 0.1 cm and 10 cm, alternatively, between about 2 cm and 8 cm. Desirably in one embodiment, the topsheet layer separation width W5 or distance between the lateral edge 28 of the liquid permeable first topsheet layer 26 and the lateral edge of the liquid permeable second topsheet layer 13 (or absorbent article) 14 is between about 0.1 cm and 3 cm, alternatively, between about 0.1 cm and 1.5 cm.

An alternative embodiment of a sanitary pad 10 shown in top perspective view, is illustrated in FIG. 2. As seen in the figure, the embodiment includes wings 15 that are in a folded-under configuration, as they would be folded about the crotch side edges of a user's undergarment. The skin-contacting (user-facing) first topsheet layer surface 26A is in an elevated or floating state above the pad lower portion 100 (and specifically, the liquid permeable second topsheet layer 20). Two opposing longitudinal direction end openings 50 are defined by four opposing longitudinal direction end lobes 27, and are attached to the liquid permeable second topsheet layer 20 at four discrete attachment zones 52 highlighted by a series of parallel stripes. The four lobes 27 are of similar profile shape as portions of the absorbent article ends 11, 12, and as the underlying liquid permeable second topsheet layer 20 (and liquid impermeable backsheet layer 22) of which they overlap. Circular visual elements 76 can be seen through the centrally positioned opening 30 of the liquid permeable first topsheet layer 26. The circular visual elements 76, which can be seen from the underlying liquid permeable second topsheet layer 20, are configured to be limited in overall dimension to that of the centrally positioned opening 30 dimensions. They are illustrated arranged in an overall oval shape. As noted, this need not always be the case.

A further alternative embodiment of a sanitary pad is shown in top perspective view in FIG. 2A. As can be seen in this figure, a differently shaped pad includes an elevated liquid permeable first topsheet layer 26, and includes wings 15 that are extending outwardly from the absorbent article opposing lateral side edges. While the liquid permeable first topsheet layer 26 is partially similar in shape to that of the liquid permeable second topsheet layer 20, its end edges 27 are not ornamental or scalloped as in the previous embodiment, but merely mimic the simple curved profile edge of the underlying layers. The first topsheet layer 26 is also of noticeably narrower width than that of the underlying second topsheet layer 20. In the embodiments shown in FIGS. 1, 2, 2A, and 2B, air circulation is encouraged across the liquid permeable first topsheet layer 26 surfaces, along all edges of the absorbent article 10 through ventilation/end openings 50 and lateral side edge openings. The air-circulation is illustrated schematically by the circular arrows.

Still a further alternative embodiment of a sanitary pad 10 is shown in top perspective view in FIGS. 2B and 2E. As can be seen in these figures, additional (and optional) side barrier walls 53 are included along each opposing lateral side edge of the absorbent article 10 so as to create liquid control barriers adjacent the central fluid insult region of the sanitary pad 10. The additional side barrier walls 53 may be formed from nonintegral (separate) materials (FIG. 2B) that are bonded between the upper surfaces of the liquid permeable second topsheet layer 20 or wings 15, to the opposing lateral side edges 28 of the liquid permeable first topsheet layer 26, or alternatively to the underside (garment-facing surface) of the liquid permeable first topsheet layer 26B. Alternatively, such additional side barrier walls 53 may be integral extensions (FIG. 2E) of the liquid permeable first topsheet layer 26 that extend downward to a subjacent layer (such as 20). Such barriers may also include additional hydrophobic treatments or additional barrier layers. Such additional side barrier walls 53 may be of a single layer or multiple layer construction, and are desirable made of either a hydrophobic or liquid impermeable material with similar extensibility as the first topsheet layer, so as to block or slow the lateral flow of liquid off the opposing lateral side edges 13, 14 of the absorbent article, especially in the wing 15 areas, but which allow for expansion during a user's movements. Such additional side barrier walls 53 desirably are configured to extend generally vertically upward (along the Z direction) from the adjacent wing 15 areas to the liquid permeable first topsheet layer 26 and have a shorter length along the absorbent article longitudinal direction L than the liquid permeable first topsheet layer 26 length. In such an embodiment, air circulation is still permitted around the liquid permeable first topsheet layer 26 along all four side edges of the absorbent article 10, but in a more limited fashion than in the embodiment shown in FIGS. 1 and 2. Such barrier walls 53 may themselves be extensible or elastic so as to allow for expansion (and or retraction) during prolonged article use. Such limited side barrier walls 53, may be of the same length as the length of the wings, along the article longitudinal direction. While not shown in the figures, such side barriers may also include Z-folds to allow for their expansion during use.

Still in yet a further alternative embodiment of a sanitary pad 10, as seen in FIG. 2C, such additional side barrier walls 54 may extend the entire length or a substantial portion (greater than 50%, alternatively greater than 80%, alternatively, greater than 90%) of the length of the cupped absorbent article 10 or liquid permeable first topsheet layer 26 (if of different cupped lengths) along the longitudinal direction L. In such an embodiment, the additional side barrier walls 54 may act to totally enclose a void space between the liquid permeable first 26 and second 20 topsheet layers, except for the end openings 50. In this fashion, air circulation is still permitted at least about the liquid permeable first topsheet layer 26 at the absorbent article opposing longitudinal ends 11, 12, such as at the two article end edges rather than the four sides of the previous article embodiments. It should be recognized, that if the barrier walls 53, 54 are fashioned of a hydrophobic material such could also provide for breathability along the lateral side edges of the absorbent article. Further, in an alternative embodiment, if such barrier walls 53, 54 are fashioned from a liquid impermeable material or include an additional liquid impermeable layer attached thereto, they may optionally also be provided with breathability, regardless of their ability to pass liquids.

As seen in the top plan view of FIG. 2D, a further alternative embodiment of the pad 10 includes a liquid permeable first topsheet layer 26 with opposing longitudinal direction ends 27 that are located on the liquid permeable second topsheet layer at a position inwardly from the opposing longitudinal direction ends 11, 12 of the absorbent article 10 and also the opposing longitudinal direction ends 101 of the liquid permeable second topsheet layer 20. The attachment zones 52 are limited to discrete areas at the ends 27. The ends 27 and attachment zones 52 are configured to include similar shape portions as those of the subjacent liquid permeable second topsheet layer 20 (and backsheet layer). While in all embodiments shown, the length L2 of the relaxed liquid permeable first topsheet layer 26 is shorter than that L7 of the absorbent article lower portion 100, in the embodiment shown in FIG. 2D, the length L2 is even relatively shorter than in prior embodiments.

Figure 4:
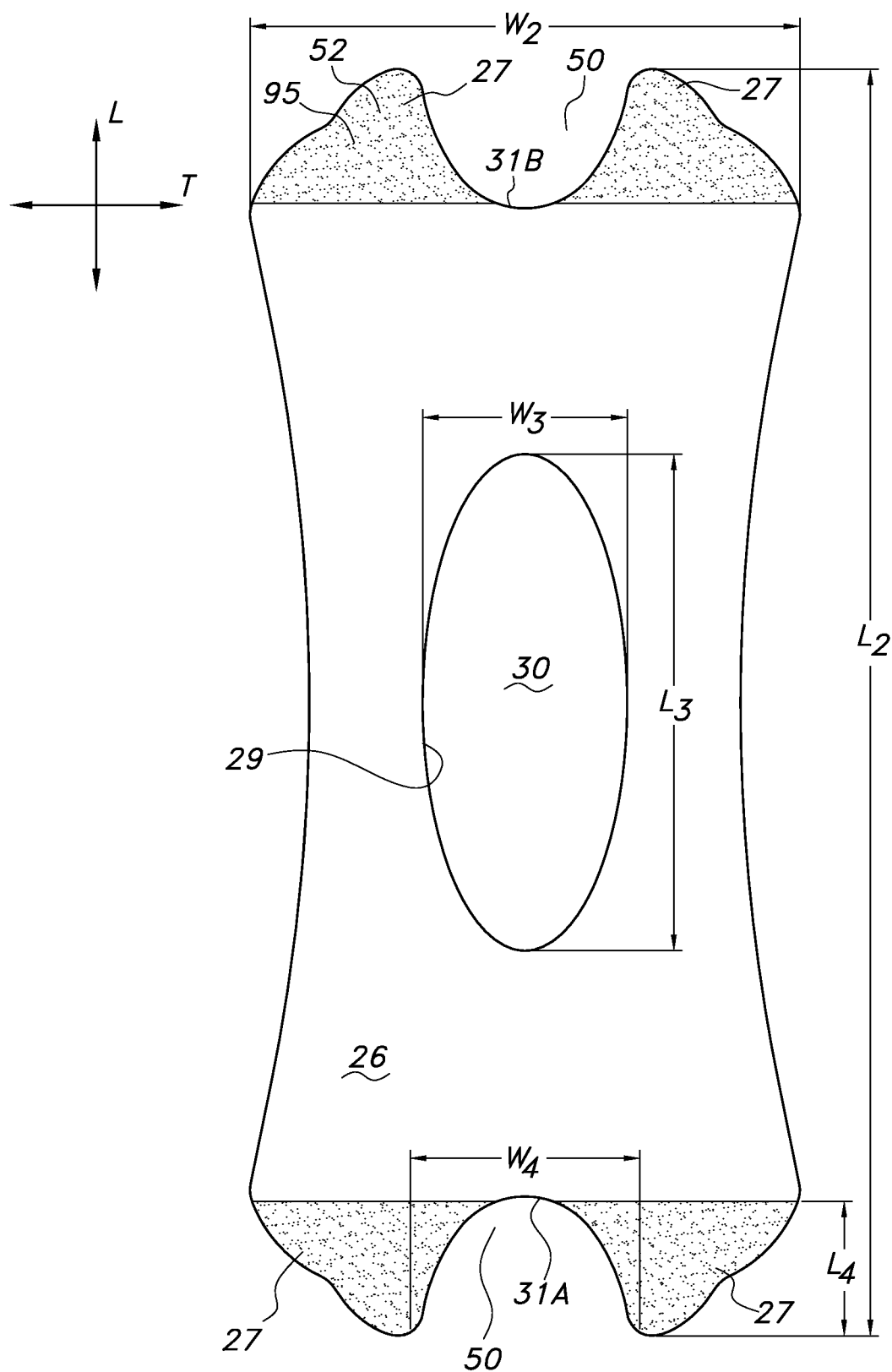
FIG. 4 illustrates a top plan view of an alternative, elevated skin-contacting first topsheet layer.

A plan view of an alternative embodiment of a liquid permeable first topsheet layer 26 is shown in FIG. 4. As can be seen in the figure, the opposing longitudinal direction ends 27 of the liquid permeable first topsheet layer 26 includes adhesive areas 95 as a bonding agent in the attachment zones 52. An exploded cross-sectional view of the absorbent article 10 of FIG. 1 is shown in FIG. 5. As can be seen in the figure, attachment adhesive 110 is positioned on the underside surfaces of the wings 15 and central longitudinal direction of the backsheet layer (as well as an adhesive release sheet 111) for attachment of the absorbent article 10 to an undergarment in use.

The liquid permeable first topsheet layer 26 may be made from a variety of extensible or elastic materials. Such layer may be of a single layer or multiple layer laminate material. Such liquid permeable first topsheet layer does not include a storage component attached directly thereto, so that liquid/fluid waste is not retained in a core-like layer directly adjacent the user's body during prolonged absorbent article use. Such layer is desirably in one embodiment, of an elastic laminate material.

In one embodiment, such first topsheet layer demonstrates inherent hydrophobicity based on the polymeric materials contained in the layer (as opposed to topical treatments). Alternatively, such layer demonstrates hydrophobicity based on treatments made to the layer, such as for example, hydrophobic surface treatments. Such treatments are well known in the art and will therefore not be further described. Alternatively, all materials making up the layer 26 are inherently hydrophobic, such as being made from elastic synthetic polymers and nonelastic synthetic polymers, such as from polyolefinic and styrenic block copolymers, alternatively a layer formed from a stretch bonded laminate. Alternatively, such layer may be treated to impart partial hydrophobicity thereto.

The liquid permeable first topsheet layer 26 may be manufactured from any number of conventional extensible or elastic materials as long as they provide extensible or elastic functionality along the article longitudinal direction. For instance, non-limiting examples of such materials include foams (such as open-celled foams), fibrous nonwoven sheet materials, such as spunbond, spunlace, meltblown, and carded web materials (such as thermally bonded carded webs (TBCW), through-air bonded carded webs (TABCW)), fibrous woven sheet materials, apertured film materials, and laminate combinations of the foregoing materials.

One suitable material is a stretch bonded laminate (SBL) where the elastic core or middle layer is elongated before two opposing outer nonwoven layers are attached. Such materials may be normally produced to provide elastic functionality along a machine direction. However, if an elastic laminate is normally produced to provide elastic functionality along a cross-machine direction, the laminate may be rotated 90 degrees prior to placement within the article, so as to impart elastic performance along the desired, article longitudinal direction.

Another suitable material is a necked-bonded laminate (NBL). The NBL material is also a three-layer laminate but the elastic core or middle layer is not pre-stretched prior to being attached to the two outer nonwoven layers. Instead, the opposing outer layers are necked-stretched before the elastic core or middle layer is attached to them. Other more specific examples of such elastic materials that can be used for the liquid permeable first topsheet layer 26 include a continuous filament stretch bonded laminate (CFSBL), a vertical filament stretch bonded laminate (VFL), a necked stretch bonded laminate (NSBL) or a necked thermal laminate (NTL), an elastic meltblown-based, stretch laminate, an elastic film-based, stretch laminate, and a pre-formed elastic strand or yarn-based, stretch laminate. Combinations of the above materials can also be used. Such materials are described for example in U.S. Pat. No. 4,720,415 to Vander Wielen et al., U.S. Pat. No. 5,366,793 to Fitts et al., U.S. Pat. No. 5,385,775 to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. An elastic fiber/yarn-based, nonwoven laminate may also be employed as the first topsheet layer 26. Such a layer may include pre-formed elastic sheets (i.e. spandex-type materials), or those polyester-polyurethane copolymer fibers in elongated strand form, commonly sold under the LYCRA brand, that are then adhesively bonded to one or more hydrophobic nonwoven layers when such fibers are in a stretched condition. Following bonding and upon retraction, the nonwoven layer forms gathers as would occur with the previously described laminates as well.

Desirably nonwoven laminates will typically include either an extensible layer or elastic layer, and at least one surface bonded nonwoven layer such as a meltblown, spunbond or through-air bonded web. The various extensible or elastic materials are placed in the absorbent article structure such that they provide extensibility or elasticity along the absorbent article longitudinal direction (which may also be the article production machine direction). Such materials may be placed in the absorbent article while in a pre-stretched or pretensioned condition, such that after attachment to the lower portion 100 of the absorbent article (such as the liquid permeable second topsheet layer 20), the retraction of the layer causes the ends of the absorbent article to curve outwardly and/or upwardly, and desirably not curl over the first topsheet layer when the article is in a relaxed and opened (unfolded) state.

Alternatively, elastic materials may be bonded to the article without being pre-stretched, but the shorter length of the liquid permeable first topsheet layer 26, causes the absorbent article lower portion to take on the curved configuration (with spatial gap between topsheet layers) after the ends of the first topsheet are attached to the ends of the absorbent article/second topsheet layer. Again, as with prior embodiments, such nontensioned extensible or elastic first topsheet layer is not desirably in one embodiment, so short with respect to the relaxed absorbent article lower portion 100 length, that it causes the formed (and relaxed) cupped-article ends to curl or curve over themselves, or over the user-facing surface of the first topsheet layer 26 when the article is in a relaxed condition.

Elastic materials that may specifically be used in the first topsheet layer 26 include for example polyolefinic, or styrenic block copolymer-based materials. If the liquid permeable first topsheet layer is extensible rather than elastic, such layer desirably does not demonstrate an extensibility that allows for an ultimate elongation that would result in its length extending to the same length (relaxed) as the second liquid permeable topsheet layer 20 while the article is being stored prior to use.

Such topsheet layer 26 may also be further apertured, embossed and/or treated in order to impart desired attributes to the liquid permeable first topsheet layer 26. Examples of additional treatments include application of skin health agents, coloring agents, odor control agents, stain masking agents, further hydrophobic agents, and the like. In one embodiment, the liquid permeable first topsheet layer 26 is desirably a stretch-bonded laminate of a spunbond material laminated to both sides of an apertured elastic film, such as the materials described in the previously noted Siquiera reference. Further, extensible and/or elastic, permeable topsheet materials are also described in U.S. Pat. No. 8,383,877 to Singh Kainth et al., which is hereby incorporated by reference thereto in its entirety, for purposes not inconsistent herewith.

The liquid permeable second topsheet layer 20 may be made from natural fibers, or similar materials as previously described with respect to the liquid permeable first topsheet layer 26. However, such liquid permeable second topsheet layer 20 is desirably inherently hydrophilic or has been treated so as to impart some level of hydrophilicity, alternatively, such that it is more hydrophilic than said liquid permeable first topsheet layer. Such hydrophilicity may be imparted by readily available surfactants as are commonly known in the art, and will therefore not further be described. The relaxed length of the liquid permeable second topsheet layer 20 is desirably larger than that of the liquid permeable first topsheet layer 26, desirably with the ends of the two layers bonded at attachment zones.

As seen in the figures, the liquid permeable second topsheet layer 20 may also be made from two or more different nonwoven or film materials at least one of which is inherently hydrophilic or which has been treated to provide such property, with the different materials placed in separate locations transversely across the second topsheet layer 20 and along the absorbent article transverse direction. For example, the liquid permeable second topsheet layer 20 may be a two layer (such as in the same or two different horizontal planes) or multi-component material with a central longitudinally directed topsheet section positioned along and straddling the central longitudinal direction of the article, with lateral side-topsheet sections flanking and joined to each side (or side longitudinal edge) of the central longitudinally directed topsheet layer section. The central topsheet section may be made for example, from the aforementioned TABCW materials or it may be made from a perforated film that has been treated to be hydrophilic. The lateral side topsheet sections may be made from a different fibrous nonwoven material which is joined to the central longitudinally directed section, such as by adhesive or thermal bonding. Such a two layer topsheet configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. The liquid permeable second topsheet layer 20 is desirably in one embodiment apertured TABCW or apertured PE film. Suitable liquid permeable second topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety.

The basis weight of nonwoven webs to be used as liquid permeable first or second topsheet layers may generally vary, such as for example from about 5 grams per square meter ("gsm") to 200 gsm, in some embodiments from about 5 gsm to about 150 gsm, alternatively from about 10 gsm to about 125 gsm, and in some embodiments, from about 15 gsm to about 120 gsm.

As noted in the figures, subjacent the liquid permeable second topsheet layer 20 in the article depth direction Z, may be positioned one or more interiorly situated liquid handling layers and absorbent core layers (the absorbent core layers being storage components) designed to respectively transport or retain body exudates that have passed through the topsheet layers to the absorbent article interior. Optionally, although not shown in the figures, in an alternative embodiment a fluid transfer layer may be attached to the garment-facing surface 26B of the liquid permeable first topsheet layer 26. Such additional fluid transfer layer would desirably include openings of the same shape and size that are aligned with the openings of the liquid permeable first topsheet layer 26 and can be comprised of bonded carded webs, hydroentangled nonwoven webs, or spunbond webs for example. It is desirable that such optional fluid transfer layer be hydrophobic either inherently, based on the polymer composition of such layer, or alternatively treated to impart hydrophobicity to it.

The absorbent core layer 23C and liquid handling layer(s) can themselves comprise a single layer or multiple layers and these one or more layers can comprise similar or different materials. Highly absorbent core layers that are used as storage components often include, but are not limited to, batts or webs containing wood pulp fibers, superabsorbent particles or fibers (also known as SAP or SAM), synthetic wood pulp fibers, synthetic fibers, coform materials, and combinations thereof. The absorbent core layer 23C may comprise any one of a number of materials and structures, the particular selection of which will vary with the desired loading capacity, flexibility, body fluid to be absorbed and other factors known to those skilled in the art. By way of example, suitable materials and/or structures for the absorbent core layers include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States Patent Publication 2010/0174260 to Di Luccio et al., each of which is hereby incorporated by reference thereto in its entirety.

The shape of the absorbent core layer can vary as desired and can comprise any one of various shapes including, but not limited to, generally triangular, rectangular, dog-bone and elliptical shapes. In one embodiment, the absorbent core layer has a shape that generally corresponds with the overall peripheral shape of the absorbent article such that the absorbent core layer(s) terminates proximate the peripheral seal region 35. The dimensions of the absorbent core layer can be substantially similar to those of the overall absorbent article, however it will be appreciated that the dimensions of the absorbent core layer while similar, will often be slightly less than those of the overall absorbent article in order to be adequately contained therein, and desirably sealed around the edges. In one embodiment, the absorbent core layer is a hydrophilic spunlace web material, having a basis weight of between about 20 and 80 gsm, alternatively between about 30 and 80 gsm, alternatively between about 30 and 50 gsm. Such absorbent core layer may in one embodiment, be constructed of a blend of synthetic fibers in a spunlace web such as for example, a blend of PET and rayon fibers, or alternatively, a homogeneous layer of 100 percent rayon fibers, air-laid materials, or foam rubber materials that are treated to be hydrophilic as needed.

In a further alternative embodiment, the one or more absorbent core layers 23 can be sealed between the liquid permeable second topsheet layer 20 and the liquid impermeable backsheet layer 22 at the perimeter of the one or more absorbent core layers along a peripheral seal region formed by the application of heat and pressure to melt thermoplastic polymers located in the liquid permeable second topsheet layer 20 and/or liquid impermeable backsheet layer 22. Desirably, in one embodiment, the liquid permeable second topsheet 20 layer is bonded at least at its periphery, to the liquid impermeable backsheet layer 22 at least in the peripheral seal region 35, but may also be bonded to it at other locations inward of the peripheral seal region.

The liquid impermeable backsheet layer 22 functions to isolate absorbed fluids from the wearer's garments or bedding, and therefore desirably can comprise a variety of liquid-impervious materials. In one aspect, the liquid impermeable backsheet layer 22 may optionally comprise a material that prevents the passage of liquids but allows air and water-vapor to pass there-through. The liquid impermeable backsheet layer 22 can comprise a single layer or multiple layers, and these one or more layers can themselves comprise similar or different materials. Suitable liquid impermeable backsheet layer materials include, but are not limited to, polyolefin films, nonwovens, nonwoven laminates, and film/nonwoven laminates. The particular structure and composition of the liquid impermeable backsheet layer 22 may be selected from various known films and/or fabrics with the particular material being selected as appropriate to provide the desired level of liquid barrier, strength, abrasion resistance, tactile properties, aesthetics (such as texture and printability) and so forth. Suitable backsheet layer materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety. The liquid impermeable backsheet layer 22 may be breathable or nonbreathable, as may be desired. In one embodiment, the liquid impermeable backsheet layer is a breathable polyolefinic film having a basis weight of between about 18 and 40 gsm, alternatively between about 20 and 30 gsm, such as of a polyethylene film.

The side barrier walls 53, 54 may be extensions of either the liquid permeable first topsheet layer 26 or the liquid permeable second topsheet layer 20. Alternatively, such barrier structures may be constructed of different materials, such as hydrophobic or liquid impermeable nonwoven or film materials (as previously described) that can assist in preventing the leakage of liquid/fluid off the opposing lateral side edges of the absorbent article. Such side barrier walls 53, 54 may themselves be extensible or elastic, or alternatively may include surface folds (not shown) to allow the preferential bending of their structures during use, such as would occur with Z-folds.

As noted, the absorbent articles of the invention may include other additional features as are generally known in the art. Such features may include wing or tab-like features 15, which are desirably extensions of the liquid permeable second topsheet layer 20 and liquid impermeable backsheet layer 22 that extend out from the opposing lateral side edges 13, 14 of the article 10. Such wings may also be non-integral in construction, either being attached to the second topsheet layer 20 or the backsheet layer 22.

The articles may further be individually wrapped in a pouch, such as those which are commonly known in the art. In such an instance, such article may be releasably fastened to the inside surface of such pouch for ease of article handling and eventual disposal.

In a first example of an absorbent article that may be made in accordance with the disclosure, a liquid permeable first topsheet layer may be formed from an apertured elastic film-based, stretch-bonded laminate made in accordance with Siqueira, and available from the Kimberly-Clark Corporation. Such material demonstrates machine-direction elongation and retraction capability and a can be placed along an article longitudinal direction such that the machine-direction elongation extends along the article longitudinal direction. In a second example, a liquid permeable first topsheet layer may be made from an elastic fiber-based laminate, such as that available from NPS Corporation of Green Bay, Wis. under the designation STRATAFLEXX 135 GSM (EM-33750). Such an elastic fiber-based laminate may be a cross-direction stretch, tri-laminate nonwoven material having a sandwiched elastic fiber core between two 30 gsm, PP/PET spunlace outer layers. The NPS material may be rotated 90 degrees before bonding onto an absorbent article as the first topsheet layer, such that it provides for article stretch along the article longitudinal direction.

In each example, such first topsheet layers desirably include a length between opposing longitudinal ends of about 214 mm, a lateral width at its widest point of about 99 mm, a centrally positioned, cut-out oval opening of a length of about 91 mm, and having a width of about 38 mm, two opposing longitudinal direction end openings of semicircular configuration, having a length of about 26 mm and width of about 47 mm. The second topsheet layer in such examples would have a length of about 240 mm and a width of between about 80 mm and 110 mm (and include additional side cover sections as previously described). In either example, such first topsheet layers would be bonded at or adjacent their longitudinal ends to the longitudinal ends of a second topsheet layer, by either adhesive, thermal, or ultrasonic bond methods. In either example, such first topsheet layers would have a relaxed/contracted length shorter than that of a second topsheet layer, such that the final article would take on a curved configuration when in a relaxed condition and stretch along the article longitudinal direction when placed in use. In each of such examples, such articles would include at least one liquid handling layer and at least one absorbent core layer situated between the second topsheet layer and the backsheet layer. Examples of such article internal layers include a transfer layer subjacent to the second topsheet layer, the transfer layer having an oval aperture similar to that of the first topsheet layer and having a basis weight of between about 8 gsm and 180 gsm, an airlaid layer subjacent to the transfer layer and having a basis weight of between about 20 gsm and 260 gsm, a SAP sheet (of pulp and SAP) subjacent to the airlaid layer and having a basis weight of between about 30 and 280 gsm, and a polyolefinic film backsheet (either breathable or non-breathable) having a basis weight of between about 20 gsm and 30 gsm. The additional internal absorbent article layers, such as surge, transfer, and multiple absorbent core layers can be utilized as desired within the absorbent article of the present invention, subjacent to the second topsheet layer. Such additional layers are described for example in United States patent publication 2012/0277711 to Kim et al., and international publication WO2014/085974 to Miao Lin et al., each of which are hereby incorporated by reference thereto in its entirety, for purposes consistent herewith.

As can be seen, an absorbent article is provided with spaced-apart, two layer topsheets, without an intermediate fluid storage component between them. The spaced-apart topsheets allow for air flow between their structures as well as through and across the uppermost body contacting topsheet layer. Such is enhanced by both lateral side gaps in the article, as well as a series of end openings at the opposing longitudinal direction ends of the article. Such structure provides for both fluid acquisition quickly through uninterrupted aperture openings directly to a lower pad surface, as well as breathability and dryness over prolonged pad usage. By utilizing a relatively smaller dimensioned, and stretchable (and desirably elastic) liquid permeable first topsheet layer, compared with a subjacent second topsheet layer, an article is created that takes on and maintains a naturally curved configuration during use. Such smaller dimensioned, liquid permeable first topsheet layer can be placed directly under the fluid insult region of a user's body such that fluid passes directly through openings and apertures in the layer into the pad body. Such rapid acquisition of liquid may be enhanced by the use of multiple layers in the article with aligned macro-openings along the article depth direction Z. By separating such aligned openings with void space, rewet sensations can be reduced.

During use, the two topsheets transition from a primary phase of being separated along the majority of their entire length to occasionally being in contact with each other due to pad deformation and pad forces exerted by the user. This constant interplay between layer contact and separation assists in reducing sensations of rewet, as air circulation is provided between layers and through openings within the pad and the upper-most, user-facing surface of the pad. The extensible or elastic liquid permeable first topsheet layer allows for the layer to routinely conform to the user's body with less impact by the movement of the article lower portion with the user's undergarments. Such extensibility/elasticity allows the upper topsheet layer to demonstrate a separation predisposition during use, thereby maintaining the physical separation of topsheet layers whenever possible, and also maintaining separation of a user's body from the soiled portion of the absorbent article.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having a longitudinal direction, a transverse direction, and a depth direction, said absorbent article having absorbent article opposing first and second longitudinal direction ends, and absorbent article opposing lateral side edges extending between said absorbent article opposing first and second longitudinal direction ends, said absorbent article comprising:
   a central longitudinal direction;
   a liquid permeable first topsheet layer having a first topsheet layer relaxed length, first topsheet layer opposing longitudinal direction ends, and first topsheet layer opposing lateral side edges extending between said first topsheet layer opposing longitudinal direction ends, said liquid permeable first topsheet layer defining a centrally positioned opening and further wherein said liquid permeable first topsheet layer being extensible along at least said absorbent article longitudinal direction;
   a liquid permeable second topsheet layer subjacent to said liquid permeable first topsheet layer along said absorbent article depth direction, said liquid permeable second topsheet layer having a second topsheet layer relaxed length that is longer than said first topsheet layer relaxed length, and said liquid permeable first topsheet layer being attached by attachment zones to said liquid permeable second topsheet layer at said liquid permeable first topsheet layer opposing longitudinal direction ends; and which said liquid permeable second topsheet layer can be viewed through said liquid permeable first topsheet layer opening;
   a liquid impermeable backsheet layer subjacent to said liquid permeable second topsheet layer along the absorbent article depth direction;
   at least one absorbent core layer sandwiched between said liquid permeable second topsheet layer and said liquid impermeable backsheet layer;
   an apertured layer having a centrally positioned aperture, said apertured layer situated between said liquid permeable second topsheet layer and said absorbent core layer in the absorbent article depth direction, and further wherein said centrally positioned aperture is aligned along the absorbent article depth direction with said centrally positioned opening;
   wherein said absorbent article further includes at least two opposing longitudinal direction end openings at or adjacent said absorbent article opposing longitudinal direction ends, said longitudinal direction end openings formed by portions of said liquid permeable first topsheet layer and wherein said centrally positioned opening is selected from the group consisting of oval shaped, circular shaped, oblong, and multiple proximate openings positioned along said absorbent article central longitudinal direction between said opposing longitudinal direction end openings.

2. The absorbent article of claim 1 wherein said liquid permeable first topsheet layer is attached on said absorbent article by at least four separate attachment zones, at least two of each of said attachment zones being positioned either at or adjacent each absorbent article opposing longitudinal direction end, such that at least one end opening in said liquid permeable first topsheet layer is defined by said liquid permeable first topsheet layer at or adjacent each of said liquid permeable first topsheet layer opposing longitudinal direction ends and between said at least two attachment zones.

3. The absorbent article of claim 1, wherein said absorbent article includes a central longitudinal direction and said opposing longitudinal direction end openings number at least two which are positioned along said central longitudinal direction.

4. The absorbent article of claim 1, wherein said opposing longitudinal direction end openings are selected from curvilinear-edged, semicircular, or U-shaped opening configurations.

5. The absorbent article of claim 3, wherein said at least two opposing longitudinal direction end openings are aligned with each other along the absorbent article central longitudinal direction.

6. The absorbent article of claim 2, wherein said attachment zones are spaced inwardly from said absorbent article opposing longitudinal direction ends.

7. The absorbent article of claim 2, wherein said attachment zones are spaced inwardly of said liquid permeable second topsheet layer opposing longitudinal direction ends.

8. The absorbent article of claim 1, wherein said liquid permeable first topsheet layer and said liquid permeable second topsheet layer each include peripheral edges at or adjacent the absorbent article opposing longitudinal direction ends, which peripheral edges are of generally similar shape for each of the liquid permeable first and second topsheet layers.

9. The absorbent article of claim 8, wherein the peripheral edges of each topsheet layer at or adjacent the absorbent article opposing longitudinal direction ends are of generally the same size.

10. The absorbent article of claim 1 wherein said centrally positioned opening and said centrally positioned aperture are both oval-shaped.

11. The absorbent article of claim 1, wherein said absorbent article includes more than one opposing longitudinal direction end opening defined by said liquid permeable first topsheet layer at or adjacent each of said absorbent article opposing longitudinal direction ends.

12. The absorbent article of claim 1, wherein said liquid permeable first topsheet layer is attached to a layer subjacent to the liquid permeable topsheet layer along the absorbent article depth direction, at or adjacent at least one location along said absorbent article opposing lateral side edges.

13. The absorbent article of claim 12, wherein said liquid permeable first topsheet layer is attached to a layer subjacent to the liquid permeable topsheet layer along the absorbent article depth direction, at or adjacent substantially the entire length of said absorbent article opposing lateral side edges.

14. The absorbent article of claim 1, wherein said liquid permeable first topsheet layer is elastic.

15. The absorbent article of claim 1, wherein said liquid permeable second topsheet layer is a multicomponent topsheet layer having a central topsheet section and side topsheet sections, in which said central topsheet section of said liquid permeable second topsheet layer can be seen through an opening in said liquid permeable first topsheet layer without a visual hindrance of an intermediary layer.

16. The absorbent article of claim 1, wherein said liquid permeable first topsheet layer is hydrophobic.

17. The absorbent article of claim 1, wherein a topographical visual feature on a layer subjacent the liquid permeable first topsheet layer in the absorbent article depth direction, can be seen through at least one opening of said liquid permeable first topsheet layer.

18. The absorbent article of claim 1, wherein said liquid permeable first topsheet layer is separable from said liquid permeable second topsheet layer by a distance of between about 0.01 mm and 6 mm during article use.

19. The absorbent article of claim 1, wherein said liquid permeable first topsheet layer is attached to said liquid permeable second topsheet layer only at said liquid permeable first topsheet layer opposing longitudinal ends, and said liquid permeable second topsheet layer includes a curved configuration when said absorbent article is in a relaxed configuration.

20. An absorbent article including multiple topsheet layers, a backsheet layer and an absorbent core layer sandwiched between one of said topsheet layers and said absorbent core layer comprising:
  a central longitudinal direction;
  a first planar, liquid permeable topsheet layer and a second planar, liquid permeable topsheet layer, both the first planar, liquid permeable topsheet layer and the second planar, liquid permeable topsheet layer having a substantially elongate shape with a longitudinal direction and a transverse direction, each liquid permeable topsheet layer comprising two opposing longitudinal ends;
  said first planar, liquid permeable topsheet layer being extensible and defining a centrally positioned opening and at least two opposing longitudinal end openings therein wherein the centrally positioned opening is selected from the group consisting of oval shaped, circular shaped, oblong, and multiple proximate openings positioned along said absorbent article central longitudinal direction between said opposing longitudinal end openings, whereby the second planar, liquid permeable topsheet layer is visible through said centrally positioned opening and at least two opposing longitudinal end openings;
  an apertured layer having a centrally positioned aperture, said apertured layer situated between said liquid permeable second topsheet layer and said absorbent core layer in the absorbent article depth direction, and further wherein said centrally positioned aperture is aligned along the absorbent article depth direction with said centrally positioned opening;
  said first planar, liquid permeable topsheet layer being suspended between the opposing longitudinal ends of the second planar, liquid permeable topsheet layer, whereby the two liquid permeable topsheet layers are mutually joined solely at or adjacent their opposing longitudinal ends;
  the second planar, liquid permeable topsheet layer being curved in the longitudinal direction such that a void space is present between said first planar, liquid permeable topsheet layer and said second, planar liquid permeable topsheet layer;

such that the first planar, liquid permeable topsheet layer having a length which is less than the length of the second planar, liquid permeable topsheet layer when both topsheet layers are in a relaxed state.

21. The absorbent article of claim 20, wherein the first planar, liquid permeable topsheet layer is in a pretensioned state within said absorbent article.

22. The absorbent article of claim 20, wherein the first planar, liquid permeable topsheet layer is elastic.

23. The absorbent article of claim 20, wherein the first planar, liquid permeable topsheet layer is hydrophobic and the second planar, liquid permeable topsheet layer is at least partially hydrophilic.

24. An absorbent article having a longitudinal direction, a transverse direction, and a depth direction, said absorbent article having absorbent article opposing first and second longitudinal direction ends, and absorbent article opposing lateral side edges extending between said absorbent article opposing first and second longitudinal direction ends, said absorbent article comprising:

a central longitudinal direction;

a liquid permeable first topsheet layer having first topsheet layer opposing longitudinal direction ends, and first topsheet layer opposing lateral side edges extending between said first topsheet layer opposing longitudinal direction ends, said liquid permeable first topsheet layer defining a centrally positioned opening and further wherein said liquid permeable first topsheet layer being elastic along at least said absorbent article longitudinal direction;

a liquid permeable second topsheet layer subjacent to said liquid permeable first topsheet layer along said absorbent article depth direction, said liquid permeable second topsheet layer being attached by attachment zones to said liquid permeable second topsheet layer at said liquid permeable first topsheet layer opposing longitudinal direction ends, such that said attachment of said liquid permeable first topsheet layer to said liquid permeable second topsheet layer imparts a curvature to said absorbent article towards said liquid permeable first topsheet layer; and which said liquid permeable second topsheet layer can be viewed through said liquid permeable first topsheet layer opening;

a liquid impermeable backsheet layer subjacent to said liquid permeable second topsheet layer along the absorbent article depth direction;

at least one absorbent core layer sandwiched between said liquid permeable second topsheet layer and said liquid impermeable backsheet layer;

an apertured layer having a centrally positioned aperture, said apertured layer situated between said liquid permeable second topsheet layer and said absorbent core layer in the absorbent article depth direction, and further wherein said centrally positioned aperture is aligned along the absorbent article depth direction with said centrally positioned opening;

wherein said absorbent article further includes at least two opposing longitudinal direction end openings at or adjacent said absorbent article opposing longitudinal direction ends, said longitudinal direction end openings formed by portions of said liquid permeable first topsheet and wherein said centrally positioned opening is selected from the group consisting of oval shaped, circular shaped, oblong, and multiple proximate openings positioned along said absorbent article central longitudinal direction between said opposing longitudinal direction end openings.

* * * * *